(12) United States Patent
Paesen et al.

(10) Patent No.: US 6,617,312 B1
(45) Date of Patent: Sep. 9, 2003

(54) VASOACTIVE AMINE BINDING MOLECULES

(75) Inventors: Guido Christian Paesen, Oxford (GB); Patricia Ann Nuttall, Culham (GB)

(73) Assignee: Oxford Vacs Ltd., London (GB)

( * ) Notice: Subject to any disclaimer, the term of this patent is extended or adjusted under 35 U.S.C. 154(b) by 0 days.

(21) Appl. No.: 09/618,919

(22) Filed: Jul. 18, 2000

Related U.S. Application Data

(63) Continuation of application No. 09/180,733, filed as application No. PCT/GB97/01372 on May 19, 1997, now abandoned.

(30) Foreign Application Priority Data

May 18, 1996 (GB) .............................................. 9610484
Apr. 18, 1997 (GB) .............................................. 9707844

(51) Int. Cl.⁷ .............................................. A61K 38/00
(52) U.S. Cl. ........................... 514/21; 514/2; 435/7.1; 435/325; 800/8; 800/9; 530/350; 530/300
(58) Field of Search ................................ 530/350, 300; 435/7.1, 325; 800/8, 9; 514/2, 21

(56) References Cited

FOREIGN PATENT DOCUMENTS

GB            2283239            5/1995

OTHER PUBLICATIONS

Anderson et al., 1998, Structure 6:1315–1327.
Anderson et al., 1997, Biochem. 36:4423–28.
Chinery et al., 1977, Nature 265:366–367.
Chinery et al., 1981, J. Parasitology 67:15–19.
Falus. 1994, Contents of "Histamine and Inflammation", Landes Company, Austin, pp139.
Janknecht et al., 1991, PNAS, 88:8972–76.
Jones et al., 1988, Animal Technology, 39:99–106.
Keller et al., 1993, J. Biological Chem 268:5450–5456.
Limo et al., 1993, Insect Sci. and its App. 14:235–245.
Paesen et al., 1995, Proceedings and Abstracts—The Second International Conference on Tick–Borne Pathogens at the Host–Vector Interface: a Global Perspective, pp. 317.
Ribeiro et al., 1994, J. Exp. Med. 180:2251–57.
Ribeiro, 1996, Insect Biochem. And Molecular Bio. 26:899–905.
Sun et al., 1998, Insect Biochem. And Molecular Bio. 28:191–200.
Sun et al., 1996, Thrombosis and Haemostasis 75:573–577.
Valenzuela et al., 1998, J. Exp. Bio. 201:2659–2664.
Wang et al., 1995, Parasite Immunology, 17:517–24.
Warlow et al., 1987, Molec Immun, 24:27–37.
Weichsel et al., 1998, Nature Structural Bio. 5:304–309.
Yuda et al., 1997, Euro. J. of Biochem. 249:337–342.
Zhang et al., 1998, Biochem. 37:10681–10690.
Wang et al., Parasitology, (1994), 109: 517–23.

*Primary Examiner*—Christopher S. F. Low
*Assistant Examiner*—Hope A. Robinson
(74) *Attorney, Agent, or Firm*—Klauber & Jackson

(57) ABSTRACT

A vasoactive amine binding protein (VABP) that binds to vasoactive amines with a dissociation constant of less than $10^{-7}$ M, has a sequence homology to the VABP clones male specific histamine binding protein 1 (MS-HBP1), female specific histamine binding protein 1 (FS-HBP1), female specific histamine binding protein 2 (FS-HBP2), and Dermacentor reticularis 6 (D.RET6), such that 40% or more of the amino acids of the VABP clones that are completely conserved as identical residues when said VABP clones are in alignment with each other, are still completely conserved when said VABP is included in said alignment; and that contains a sequence motif selected from the group consisting of the motif D/E A W K/R; the motif Y/C E/D L/I W; and the motifs D/E A W K/R and Y/C E/D L/I W.

17 Claims, 11 Drawing Sheets

Fig. 1

FS-HBP1

```
T3→
   1 AGAAAGCCAACATGAAGCTTCTGCTCTCTCTTGCCTTCGTCTTAGCTCTCAGCCAAGTTA   60
              M  K  L  L  L  S  L  A  F  V  L  A  L  S  Q  V  K

61 AAGCCGATAAGCCAGTTTGGGCGGATGAAGCGGCAAACGGGGAACACCAAGACGCCTGGA  120
      A  D  K  P  V  W  A  D  E  A  A  N  G  E  H  Q  D  A  W  K
         ↑

121 AGCATCTCCAAAAACTCGTTGAAGAGAATTACGACTTGATAAAAGCCACCTACAAGAACG  180
      H  L  Q  K  L  V  E  E  N  Y  D  L  I  K  A  T  Y  K  N  D

T3a→←T7c
 181 ACCCAGTTTGGGGTAACGACTTCACTTGCGTGGGTACTGCAGCGCAGAATTTGAACGAGG  240
      P  V  W  G  N  D  F  T  C  V  G  T  A  A  Q  N  L  N  E  D

241 ACGAGAAGAACGTTGAAGCATGGTTTATGTTTATGAATAATGCTGATACCGTATACCAAC  300
      E  K  N  V  E  A  W  F  M  F  M  N  N  A  D  T  V  Y  Q  H

301 ATACTTTTGAAAAGGCGACTCCTGATAAAATGTACGGTTACAATAAGGAAAACGCCATCA  360
      T  F  E  K  A  T  P  D  K  M  Y  G  Y  N  K  E  N  A  I  T

361 CATATCAAACAGAGGATGGGCAAGTTCTCACAGACGTCCTTGCATTCTCTGACGACAATT  420
      Y  Q  T  E  D  G  Q  V  L  T  D  V  L  A  F  S  D  D  N  C

421 GCTATGTCATCTACGCTCTTGGCCCAGATGGAAGTGGAGCAGGTTACGAACTCTGGGCTA  480
      Y  V  I  Y  A  L  G  P  D  G  S  G  A  G  Y  E  L  W  A  T

T3b→←T7d
 481 CCGATTACACGGATGTTCCAGCCAGTTGTCTAGAGAAGTTCAATGAGTATGCTGCAGGTC  540
      D  Y  T  D  V  P  A  S  C  L  E  K  F  N  E  Y  A  A  G  L

541 TGCCGGTACGGGACGTATACACAAGTGATTGCCTCCCAGAATAACTTGGGCATATCGTAA  600
      P  V  R  D  V  Y  T  S  D  C  L  P  E  *

601 TTTCAACTTCAAAGTGTGTTATTGTCAGCATATGTCTCGAGTGTTTGATGTAGTGCGTTC  660

661 GATGATGCCATTCATCTAGGTTTCGGGTGTTCGGTACTTTATGGTCACTGCCGACGGCCA  720

←T7
 721 GCACGAGTACTCGAAAATAAAGTATTCTGAAATCGGAAAAAAAAAAAAAA  770
```

Fig. 2

FS-HBP2

```
T3→
  1 GCCGCGACGGAACTTCGAAGGAAGTCAGCATGAAGCTTCTCATACTCTCTCTTGCCCTCG    60
                                M  K  L  L  I  L  S  L  A  L  V

61 TCCTCGCCCTCAGCCAGGTTAAGGGAAATCAGCCAGATTGGGCCGATGAAGCGGCAAATG   120
     L  L  A  L  S  Q  V  K  G  N  Q  P  D  W  A  D  E  A  A  N  G
                                 ↑

121 GTGCACACCAAGACGCCTGGAAGAGTCTGAAAGCGGACGTTGAAAACGTTTACTACATGG   180
     A  H  Q  D  A  W  K  S  L  K  A  D  V  E  N  V  Y  Y  M  V

181 TGAAGGCCACCTATAAGAATGACCCAGTGTGGGGCAATGACTTCACTTGCGTGGGTGTTA   240
     K  A  T  Y  K  N  D  P  V  W  G  N  D  F  T  C  V  G  V  M

T3b→ ←T7a
241 TGGCAAATGATGTCAACGAGGATGAGAAGAGCATTCAAGCAGAGTTTTTGTTTATGAATA   300
     A  N  D  V  N  E  D  E  K  S  I  Q  A  E  F  L  F  M  N  N

301 ATGCTGACACAAACATGCAATTCGCCACTGAAAAGGTGACTGCTGTTAAAATGTATGGTT   360
     A  D  T  N  M  Q  F  A  T  E  K  V  T  A  V  K  M  Y  G  Y

361 ACAATAGGGAAAACGCCTTCAGATACGAGACGGAGGATGGCCAAGTTTTCACAGACGTCA   420
     N  R  E  N  A  F  R  Y  E  T  E  D  G  Q  V  F  T  D  V  I

→
421 TTGCATACTCTGATGACAACTGCGATGTCATCTACGTTCCTGGCACAGACGGAAATGAGG   480
     A  Y  S  D  D  N  C  D  V  I  Y  V  P  G  T  D  G  N  E  E

←
481 AAGGTTACGAACTATGGACTACGGATTACGACAACATTCCAGCCAATTGTTTAAATAAGT   540
     G  Y  E  L  W  T  T  D  Y  D  N  I  P  A  N  C  L  N  K  F

541 TTAATGAGTACGCTGTAGGTAGGGAGACAAGGGATGTATTCACAAGTGCTTGCCTAGAGT   600
     N  E  Y  A  V  G  R  E  T  R  D  V  F  T  S  A  C  L  E  *

→                         ←
601 AATAACTTCAGAATGTCGTTCTTTCAAAGCGAAAAACCAACAATGTGAACATCGGCTTGC   660

661 TGTGCTCGACGTAGCCAGCGATAATGTTGTTTTCCTGGGTTTCTGGGTTTGGATACTTTT   720

721 AGCCACTGCCGAAGAGCTGTAAAGGTAATGAAAAATAAAATGTTCAAGAGTGTGAAAAAA   780
                                    ←T7
781 AAAAAAAAAAAA   793
```

Fig. 3

FS-HBP1

T3→

1   AAAGCACTCAACATGAAGGTTCTTTTGTTGGTTCTTGGAGCTGCTCTTTGCCAGAATGCA   60
                M  K  V  L  L  L  V  L  G  A  A  L  C  Q  N  A

61  GATGCAAACCCAACATGGGCGAACGAAGCTAAATTGGGATCCTACCAAGACGCCTGGAAG   120
     D  A  N  P  T  W  A  N  E  A  K  L  G  S  Y  Q  D  A  W  K
        ↑

121 AGCCTTCAGCAAGACCAAAACAAGAGATACTATTTGGCACAAGCGACACAAACGACTGAC   180
     S  L  Q  Q  D  Q  N  K  R  Y  Y  L  A  Q  A  T  Q  T  T  D

→
181 GGCGTATGGGGTGAAGAGTTTACTTGTGTGAGTGTTACGGCTGAGAAGATTGGAAAGAAA   240
     G  V  W  G  E  E  F  T  C  V  S  V  T  A  E  K  I  G  K  K

←
241 AAACTTAACGCTACGATCCTCTATAAAAATAAGCACCTTACTGACCTGAAAGAGAGTCAT   300
     K  L  N  A  T  I  L  Y  K  N  K  H  L  T  D  L  K  E  S  H
          ═══════════

301 GAAACAATCACTGTCTGGAAAGCATACGACTACACAACGGAGAATGGCATCAAGTACGAG   360
     E  T  I  T  V  W  K  A  Y  D  Y  T  T  E  N  G  I  K  Y  E

361 ACGCAAGGGACAAGGACGCAGACTTTCGAAGATGTCTTTGTATTCTCTGATTACAAGAAC   420
     T  Q  G  T  R  T  Q  T  F  E  D  V  F  V  F  S  D  Y  K  N

→                                          ←
421 TGCGATGTAATTTTCGTTCCCAAAGAGAGAGGAAGCGACGAGGGCGACTATGAATTGTGG   480
     C  D  V  I  F  V  P  K  E  R  G  S  D  E  G  D  Y  E  L  W

481 GTTAGTGAAGACAAGATTGACAAGATTCCCGATTGCTGCAAGTTTACGATGGCGTACTTT   540
     V  S  E  D  K  I  D  K  I  P  D  C  C  K  F  T  M  A  Y  F

→
541 GCCCAACAGCAGGAGAAGACGGTTCGTAATGTATACACTGACTCATCATGCAAACCAGCA   600
     A  Q  Q  Q  E  K  T  V  R  N  V  Y  T  D  S  S  C  K  P  A

601 CCAGCTCAGAACTGATATTCTGGTAATGCTTGAACCGTAATGGTTCGACCTGCAGTCTAG   660
     P  A  Q  N  *

661 AAACATTTACCACCATCACGGTGATTATCTTACCGTAGTTTCTTAGGTCTTGTTCTTTGA   720
                                                          ←T7
721 ATAAAATAGTTCCCTGCATTGACAAAAAAAAA   753

Fig. 4

```
T3→
  1 ATGAAGATGCAGGTAGTGCTCTTACTTACCTTTGTTAGCGCCGCCCTCGCCACTCAAGCG    60
  1  M  K  M  Q  V  V  L  L  L  T  F  V  S  A  A  L  A  T  Q  A    20

61 GAGACTACATCTGCGAAAGCAGGAGAAAACCCGCTCTGGGCGCATGAGGAACTACTTGGA   120
 21  E  T  T  S  A  K  A  G  E  N  P  L  W  A  H  E  E  L  L  G    40
                            ↑

121 AAATATCAAGATGCCTGGAAAAGCATCGATCAGGGCGTGTCGGTGACTTATGTCCTTGCA   180
 41  K  Y  Q  D  A  W  K  S  I  D  Q  G  V  S  V  T  Y  V  L  A    60
                                          →       ←
181 AAGACAACATATGAGAATGACACAGGATCATGGGGATCCCAGTTTAAGTGCCTCCAGGTA   240
 61  K  T  T  Y  E  N  D  T  G  S  W  G  S  Q  F  K  C  L  Q  V    80

241 CAAGAAATAGAAAGAAAGGAAGAAGACTATACAGTTACATCTGTTTTCACCTTTAGAAAT   300
 81  Q  E  I  E  R  K  E  E  D  Y  T  V  T  S  V  F  T  F  R  N   100

301 GCGTCTTCTCCAATCAAGTATTACAACGTGACAGAAACAGTGAAGGCCGTTTTTCAATAT   360
101  A  S  S  P  I  K  Y  Y  N  V  T  E  T  V  K  A  V  F  Q  Y   120

361 GGATACAAAAACATAAGGAATGCAATTGAATACCAAGTGGGCGGTGGACTTAACATAACC   420
121  G  Y  K  N  I  R  N  A  I  E  Y  Q  V  G  G  G  L  N  I  T   140
                                    →   ←
421 GACACGCTCATTTTCACTGATGGAGAATTATGCGATGTTTTCTATGTTCCCAATGCAGAT   480
141  D  T  L  I  F  T  D  G  E  L  C  D  V  F  Y  V  P  N  A  D   160

481 CAAGGTTGTGAGCTCTGGGTCAAAAAGAGTCACTACAAACACGTACCAGACTACTGCACG   540
161  Q  G  C  E  L  W  V  K  K  S  H  Y  K  H  V  P  D  Y  C  T   180

541 TTCGTGTTCAATGTTTTCTGTGCGAAAGACAGGAAAACCTACGATATATTTAATGAAGAA   600
181  F  V  F  N  V  F  C  A  K  D  R  K  T  Y  D  I  F  N  E  E   200

601 TGTGTTTATAACGGCGAACCCTGGCTTTAAAGGCAAAAAATCTATAAAATACGGTTTCTG   660
201  C  V  Y  N  G  E  P  W  L  *                                  220
                                                                 ←T7
661 TAGTAAGTACTAATAGCAAGTAGTTGAATAATAAAAAGATTGTAAGTGCAAAAAAAAAA   719
```

Fig. 6

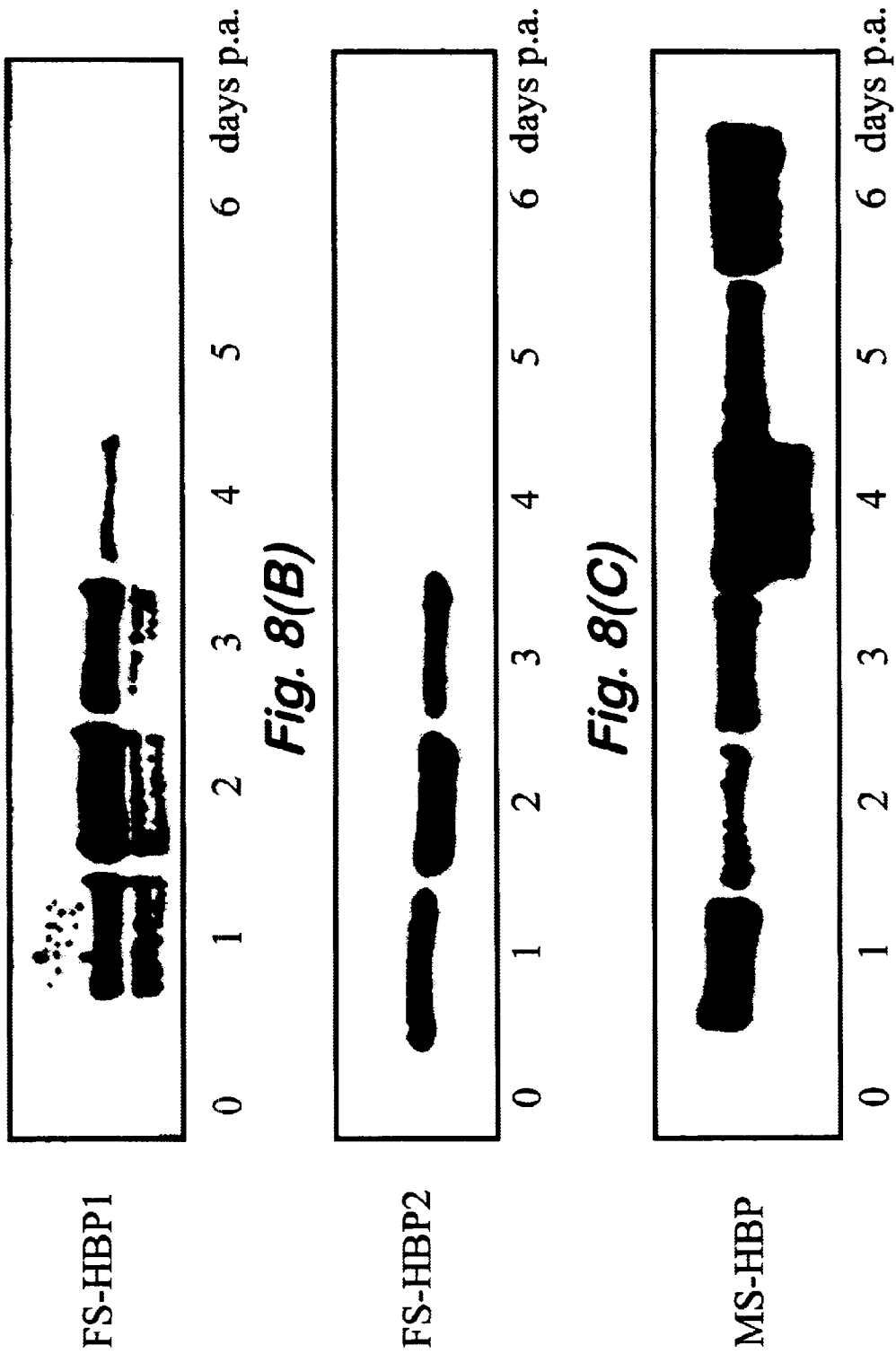

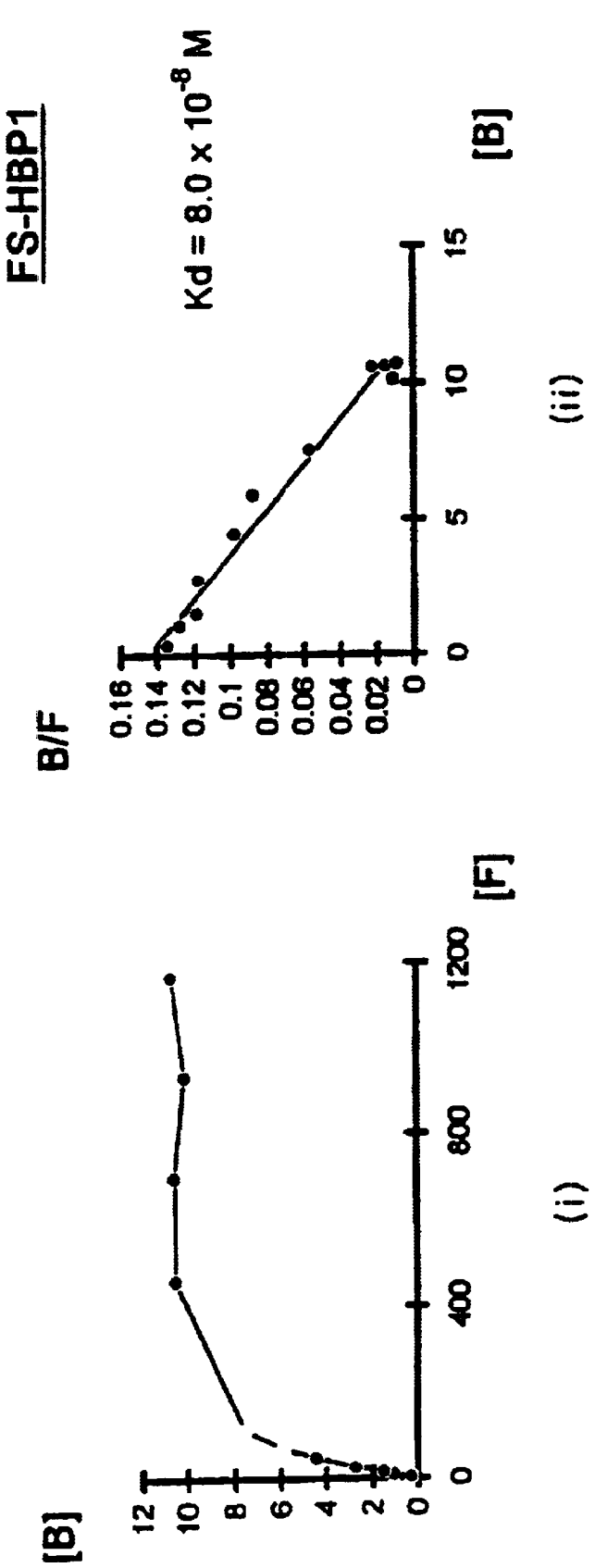

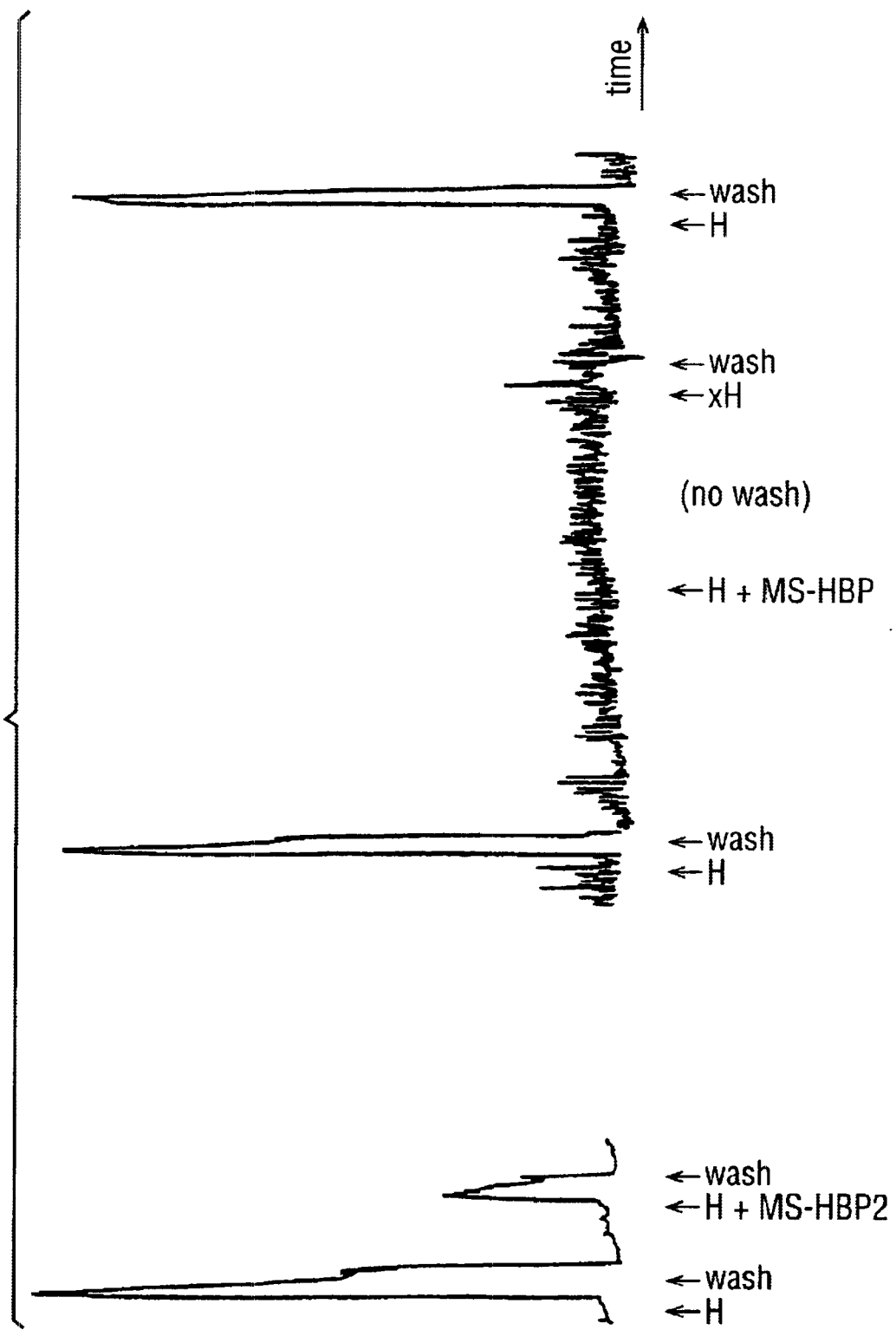

SEQUENCE LISTING

<160> NUMBER OF SEQ ID NOS: 24

<210> SEQ ID NO 1
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)...(26)
<223> OTHER INFORMATION: n = A,T,C or G

<400> SEQUENCE: 1
aayggngarc aycargaygc ntggaa                                26

<210> SEQ ID NO 2
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)...(26)
<223> OTHER INFORMATION: n = A,T,C or G

<400> SEQUENCE: 2
ktrtmrtcng tnryccanar ytcrta                                26

<210> SEQ ID NO 3
<211> LENGTH: 18
<212> TYPE: DNA
<213> ORGANISM: Artificial Sequence
<220> FEATURE:
<223> OTHER INFORMATION: primer

<400> SEQUENCE: 3
gcaggagctc ggcacgag                                         18

<210> SEQ ID NO 4
<211> LENGTH: 50
<212> TYPE: DNA
<213> ORGANISM: Artificial Sequence
<220> FEATURE:
<223> OTHER INFORMATION: primer

<400> SEQUENCE: 4
tttactagtg atggtgatga tgatggatcc cttctgggag gcaatcactt       50

<210> SEQ ID NO 5
<211> LENGTH: 26
<212> TYPE: DNA
<213> ORGANISM: Artificial Sequence
<220> FEATURE:
<223> OTHER INFORMATION: primer

<400> SEQUENCE: 5
aaggagctca gcatgaagct tctcat                                26

<210> SEQ ID NO 6
<211> LENGTH: 26
<212> TYPE: DNA
<213> ORGANISM: Artificial Sequence
<220> FEATURE:
<223> OTHER INFORMATION: primer

<400> SEQUENCE: 6
tatagatctc taggcaagca cttgtg        26

<210> SEQ ID NO 7
<211> LENGTH: 18
<212> TYPE: DNA
<213> ORGANISM: Artificial Sequence
<220> FEATURE:
<223> OTHER INFORMATION: primer

<400> SEQUENCE: 7
gcaggagctc ggcacgag        18

<210> SEQ ID NO 8
<211> LENGTH: 27
<212> TYPE: DNA
<213> ORGANISM: Artificial Sequence
<220> FEATURE:
<223> OTHER INFORMATION: primer

<400> SEQUENCE: 8
tatagatctg gttctgagct ggtgctg        27

<210> SEQ ID NO 9
<211> LENGTH: 27
<212> TYPE: DNA
<213> ORGANISM: Artificial Sequence
<220> FEATURE:
<223> OTHER INFORMATION: primer

<400> SEQUENCE: 9
tatggatcct tcacttgcgt gggtgtt        27

<210> SEQ ID NO 10
<211> LENGTH: 37
<212> TYPE: DNA
<213> ORGANISM: Artificial Sequence
<220> FEATURE:
<223> OTHER INFORMATION: primer

<400> SEQUENCE: 10
tatagcggcc gcccgggcta gtgatggtga tgatgat        37

<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11
tataggatcc gggagctcca atcagccaga ttgggc        36

<210> SEQ ID NO 12
<211> LENGTH: 37
<212> TYPE: DNA
<213> ORGANISM: Artificial Sequence
<220> FEATURE:
<223> OTHER INFORMATION: primer

<400> SEQUENCE: 12
tatagcggcc gcccgggcta gtgatggtga tgatgat        37

<210> SEQ ID NO 13

-continued

```
<211> LENGTH: 29
<212> TYPE: DNA
<213> ORGANISM: Artificial Sequence
<220> FEATURE:
<223> OTHER INFORMATION: primer

<400> SEQUENCE: 13
tatatggtac ccatcatcat caccatcac                                    29

<210> SEQ ID NO 14
<211> LENGTH: 31
<212> TYPE: DNA
<213> ORGANISM: Artificial Sequence
<220> FEATURE:
<223> OTHER INFORMATION: primer

<400> SEQUENCE: 14
atatatggta ccgttgtcgt aatccgtagt c                                 31

<210> SEQ ID NO 15
<211> LENGTH: 770
<212> TYPE: DNA
<213> ORGANISM: Rhipicephalus appendiculatus

<400> SEQUENCE: 15
agaaagccaa catgaagctt ctgctctctc ttgccttcgt cttagctctc agccaagtta    60
aagccgataa gccagtttgg gcggatgaag cggcaaacgg ggaacaccaa gacgcctgga   120
agcatctcca aaaactcgtt gaagagaatt acgacttgat aaaagccacc tacaagaacg   180
acccagtttg gggtaacgac ttcacttgcg tgggtactgc agcgcagaat ttgaacgagg   240
acgagaagaa cgttgaagca tggtttatgt ttatgaataa tgctgatacc gtataccaac   300
atacttttga aaaggcgact cctgataaaa tgtacggtta caataaggaa acgccatca   360 catatcaaac agaggatggg caagttctca cagacgtcct tgcattctct gacgacaatt   420
gctatgtcat ctacgctctt ggcccagatg gaagtggagc aggttacgaa ctctgggcta   480
ccgattacac ggatgttcca gccagttgtc tagagaagtt caatgagtat gctgcaggtc   540
tgccggtacg ggacgtatac acaagtgatt gcctcccaga ataacttggg catatcgtaa   600
tttcaacttc aaagtgtgtt attgtcagca tatgtctcga gtgtttgatg tagtgcgttc   660
gatgatgcca ttcatctagg tttcgggtgt tcggtacttt atggtcactg ccgacggcca   720
gcacgagtac tcgaaaataa agtattctga aatcggaaaa aaaaaaaaaa              770

<210> SEQ ID NO 16
<211> LENGTH: 190
<212> TYPE: PRT
<213> ORGANISM: Rhipicephalus appendiculatus

<400> SEQUENCE: 16
```

Met Lys Leu Leu Leu Ser Leu Ala Phe Val Leu Ala Leu Ser Gln Val
1               5                   10                  15

Lys Ala Asp Lys Pro Val Trp Ala Asp Glu Ala Ala Asn Gly Glu His
            20                  25                  30

Gln Asp Ala Trp Lys His Leu Gln Lys Leu Val Glu Glu Asn Tyr Asp
        35                  40                  45

Leu Ile Lys Ala Thr Tyr Lys Asn Asp Pro Val Trp Gly Asn Asp Phe
    50                  55                  60

Thr Cys Val Gly Thr Ala Ala Gln Asn Leu Asn Glu Asp Glu Lys Asn
65                  70                  75                  80

```
Val Glu Ala Trp Phe Met Phe Met Asn Asn Ala Asp Thr Val Tyr Gln
                85                  90                  95

His Thr Phe Glu Lys Ala Thr Pro Asp Lys Met Tyr Gly Tyr Asn Lys
            100                 105                 110

Glu Asn Ala Ile Thr Tyr Gln Thr Glu Asp Gly Gln Val Leu Thr Asp
            115                 120                 125

Val Leu Ala Phe Ser Asp Asp Asn Cys Tyr Val Ile Tyr Ala Leu Gly
    130                 135                 140

Pro Asp Gly Ser Gly Ala Gly Tyr Glu Leu Trp Ala Thr Asp Tyr Thr
145                 150                 155                 160

Asp Val Pro Ala Ser Cys Leu Glu Lys Phe Asn Glu Tyr Ala Ala Gly
                165                 170                 175

Leu Pro Val Arg Asp Val Tyr Thr Ser Asp Cys Leu Pro Glu
            180                 185                 190
```

<210> SEQ ID NO 17
<211> LENGTH: 793
<212> TYPE: DNA
<213> ORGANISM: Rhipicephalus appendiculatus

<400> SEQUENCE: 17

```
gccgcgacgg aacttcgaag gaagtcagca tgaagcttct catactctct cttgccctcg    60
tcctcgccct cagccaggtt aagggaaatc agccagattg gccgatgaa gcggcaaatg    120
gtgcacacca agacgcctgg aagagtctga agcggacgt tgaaaacgtt tactacatgg    180
tgaaggccac ctataagaat gacccagtgt ggggcaatga cttcacttgc gtgggtgtta    240
tggcaaatga tgtcaacgag gatgagaaga gcattcaagc agagttttg tttatgaata    300
atgctgacac aaacatgcaa ttcgccactg aaaaggtgac tgctgttaaa atgtatggtt    360
acaataggga aaacgccttc agatacgaga cggaggatgg ccaagttttc acagacgtca    420
ttgcatactc tgatgacaac tgcgatgtca tctacgttcc tggcacagac ggaaatgagg    480
aaggttacga actatggact acggattacg acaacattcc agccaattgt ttaaataagt    540
ttaatgagta cgctgtaggt agggagacaa gggatgtatt cacaagtgct tgcctagagt    600
aataacttca gaatgtcgtt ctttcaaagc gaaaaccaa caatgtgaac atcggcttgc    660
tgtgctcgac gtagccagcg ataatgttgt tttcctgggt ttctgggttt ggatactttt    720
agccactgcc gaagagctgt aaaggtaatg aaaaataaaa tgttcaagag tgtgaaaaaa    780
aaaaaaaaaa aaa                                                       793
```

<210> SEQ ID NO 18
<211> LENGTH: 190
<212> TYPE: PRT
<213> ORGANISM: Rhipicephalus appendiculatus

<400> SEQUENCE: 18

```
Met Lys Leu Leu Ile Leu Ser Leu Ala Leu Val Leu Ala Leu Ser Gln
  1               5                  10                  15

Val Lys Gly Asn Gln Pro Asp Trp Ala Asp Glu Ala Ala Asn Gly Ala
             20                  25                  30

His Gln Asp Ala Trp Lys Ser Leu Lys Ala Asp Val Glu Asn Val Tyr
         35                  40                  45

Tyr Met Val Lys Ala Thr Tyr Lys Asn Asp Pro Val Trp Gly Asn Asp
     50                  55                  60

Phe Thr Cys Val Gly Val Met Ala Asn Asp Val Asn Glu Asp Glu Lys
 65                  70                  75                  80
```

```
Ser Ile Gln Ala Glu Phe Leu Phe Met Asn Asn Ala Asp Thr Asn Met
                85                  90                  95

Gln Phe Ala Thr Glu Lys Val Thr Ala Val Lys Met Tyr Gly Tyr Asn
            100                 105                 110

Arg Glu Asn Ala Phe Arg Tyr Glu Thr Glu Asp Gly Gln Val Phe Thr
        115                 120                 125

Asp Val Ile Ala Tyr Ser Asp Asp Asn Cys Asp Val Ile Tyr Val Pro
    130                 135                 140

Gly Thr Asp Gly Asn Glu Glu Gly Tyr Glu Leu Trp Thr Thr Asp Tyr
145                 150                 155                 160

Asp Asn Ile Pro Ala Asn Cys Leu Asn Lys Phe Asn Glu Tyr Ala Val
                165                 170                 175

Gly Arg Glu Thr Arg Asp Val Phe Thr Ser Ala Cys Leu Glu
            180                 185                 190
```

<210> SEQ ID NO 19
<211> LENGTH: 753
<212> TYPE: DNA
<213> ORGANISM: Rhipicephalus appendiculatus

<400> SEQUENCE: 19

```
aaagcactca acatgaaggt tcttttgttg gttcttggag ctgctctttg ccagaatgca      60
gatgcaaacc caacatgggc gaacgaagct aaattgggat cctaccaaga cgcctggaag    120
agccttcagc aagaccaaaa caagagatac tatttggcac aagcgacaca aacgactgac    180
ggcgtatggg gtgaagagtt tacttgtgtg agtgttacgg ctgagaagat tggaaagaaa    240
aaacttaacg ctacgatcct ctataaaaat aagcacctta ctgacctgaa agagagtcat    300
gaaacaatca ctgtctggaa agcatacgac tacacaacgg agaatggcat caagtacgag    360
acgcaaggga caaggacgca gactttcgaa gatgtctttg tattctctga ttacaagaac    420
tgcgatgtaa ttttcgttcc caagagagag ggaagcgacg agggcgacta tgaattgtgg    480
gttagtgaag acaagattga caagattccc gattgctgca gtttacgat ggcgtacttt    540
gcccaacagc aggagaagac ggttcgtaat gtatacactg actcatcatg caaaccagca    600
ccagctcaga actgatattc tggtaatgct gaaccgtaa tggttcgacc tgcagtctag    660
aaacatttac caccatcacg gtgattatct taccgtagtt tcttaggtct tgttctttga    720
ataaaatagt tccctgcatt gacaaaaaaa aaa                                 753
```

<210> SEQ ID NO 20
<211> LENGTH: 200
<212> TYPE: PRT
<213> ORGANISM: Rhipicephalus appendiculatus

<400> SEQUENCE: 20

```
Met Lys Val Leu Leu Val Leu Gly Ala Ala Leu Cys Gln Asn Ala
1               5                   10                  15

Asp Ala Asn Pro Thr Trp Ala Asn Glu Ala Lys Leu Gly Ser Tyr Gln
            20                  25                  30

Asp Ala Trp Lys Ser Leu Gln Gln Asp Gln Asn Lys Arg Tyr Tyr Leu
        35                  40                  45

Ala Gln Ala Thr Gln Thr Thr Asp Gly Val Trp Gly Glu Glu Phe Thr
    50                  55                  60

Cys Val Ser Val Thr Ala Glu Lys Ile Gly Lys Lys Leu Asn Ala
65                  70                  75                  80
```

```
Thr Ile Leu Tyr Lys Asn Lys His Leu Thr Asp Leu Lys Glu Ser His
                85                  90                  95

Glu Thr Ile Thr Val Trp Lys Ala Tyr Asp Tyr Thr Thr Glu Asn Gly
            100                 105                 110

Ile Lys Tyr Glu Thr Gln Gly Thr Arg Thr Gln Thr Phe Glu Asp Val
        115                 120                 125

Phe Val Phe Ser Asp Tyr Lys Asn Cys Asp Val Ile Phe Val Pro Lys
    130                 135                 140

Glu Arg Gly Ser Asp Glu Gly Asp Tyr Glu Leu Trp Val Ser Glu Asp
145                 150                 155                 160

Lys Ile Asp Lys Ile Pro Asp Cys Cys Lys Phe Thr Met Ala Tyr Phe
                165                 170                 175

Ala Gln Gln Glu Lys Thr Val Arg Asn Val Tyr Thr Asp Ser Ser
            180                 185                 190

Cys Lys Pro Ala Pro Ala Gln Asn
        195                 200
```

<210> SEQ ID NO 21
<211> LENGTH: 719
<212> TYPE: DNA
<213> ORGANISM: Dermacentor reticulatus

<400> SEQUENCE: 21

```
atgaagatgc aggtagtgct cttacttacc tttgttagcg ccgccctcgc cactcaagcg      60
gagactacat ctgcgaaagc aggagaaaac ccgctctggg cgcatgagga actacttgga     120
aaatatcaag atgcctggaa aagcatcgat cagggcgtgt cggtgactta tgtccttgca     180
aagacaacat atgagaatga cacaggatca tggggatccc agtttaagtg cctccaggta     240
caagaaatag aaagaaagga agaagactat acagttacat ctgttttcac ctttagaaat     300
gcgtcttctc aatcaagta ttacaacgtg acagaaacg tgaaggccgt ttttcaatat       360
ggatacaaaa acataaggaa tgcaattgaa taccaagtgg gcggtggact aacataacc      420
gacacgctca ttttcactga tggagaatta tgcgatgttt ctatgttcc aatgcagat       480
caaggttgtg agctctgggt caaaaagagt cactacaaac acgtaccaga ctactgcacg     540
ttcgtgttca atgttttctg tgcgaaagac aggaaaacct acgatatatt taatgaagaa     600
tgtgtttata acggcgaacc ctggctttaa aggaccccccc tctataaaat acggtttctg    660
tagtaagtac taatagcaag tagttgaata ataaaaagat tgtaagtgca aaaaaaaaa     719
```

<210> SEQ ID NO 22
<211> LENGTH: 209
<212> TYPE: PRT
<213> ORGANISM: Dermacentor reticulatus

<400> SEQUENCE: 22

```
Met Lys Met Gln Val Val Leu Leu Thr Phe Val Ser Ala Ala Leu
 1               5                  10                  15

Ala Thr Gln Ala Glu Thr Thr Ser Ala Lys Ala Gly Glu Asn Pro Leu
            20                  25                  30

Trp Ala His Glu Glu Leu Leu Gly Lys Tyr Gln Asp Ala Trp Lys Ser
        35                  40                  45

Ile Asp Gln Gly Val Ser Val Thr Tyr Val Leu Ala Lys Thr Thr Tyr
    50                  55                  60

Glu Asn Asp Thr Gly Ser Trp Gly Ser Gln Phe Lys Cys Leu Gln Val
65                  70                  75                  80
```

```
Gln Glu Ile Glu Arg Lys Glu Glu Asp Tyr Thr Val Thr Ser Val Phe
                85                  90                  95

Thr Phe Arg Asn Ala Ser Ser Pro Ile Lys Tyr Tyr Asn Val Thr Glu
                100                 105                 110

Thr Val Lys Ala Val Phe Gln Tyr Gly Tyr Lys Asn Ile Arg Asn Ala
            115                 120                 125

Ile Glu Tyr Gln Val Gly Gly Leu Asn Ile Thr Asp Thr Leu Ile
        130                 135                 140

Phe Thr Asp Gly Glu Leu Cys Asp Val Phe Val Pro Asn Ala Asp
145                 150                 155                 160

Gln Gly Cys Glu Leu Trp Val Lys Lys Ser His Tyr Lys His Val Pro
                165                 170                 175

Asp Tyr Cys Thr Phe Val Phe Asn Val Phe Cys Ala Lys Asp Arg Lys
                180                 185                 190

Thr Tyr Asp Ile Phe Asn Glu Glu Cys Val Tyr Asn Gly Glu Pro Trp
            195                 200                 205

Leu

<210> SEQ ID NO 23
<211> LENGTH: 4
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: (1)...(1)
<223> OTHER INFORMATION: Xaa = Asp or Glu
<220> FEATURE:
<221> NAME/KEY: VARIANT
<222> LOCATION: (4)...(4)
<223> OTHER INFORMATION: Xaa = Lys or Arg

<400> SEQUENCE: 23

Xaa Ala Trp Xaa
 1

<210> SEQ ID NO 24
<211> LENGTH: 4
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: (1)...(1)
<223> OTHER INFORMATION: Xaa = Tyr or Cys
<220> FEATURE:
<221> NAME/KEY: VARIANT
<222> LOCATION: (2)...(2)
<223> OTHER INFORMATION: Xaa = Glu or Asp
<220> FEATURE:
<221> NAME/KEY: VARIANT
<222> LOCATION: (3)...(3)
<223> OTHER INFORMATION: Xaa = Leu or Ile

<400> SEQUENCE: 24

Xaa Xaa Xaa Trp
 1
```

VASOACTIVE AMINE BINDING MOLECULES

This Application is a Continuation of application Ser. No. 09/180,733, filed Nov. 13, 1998 now abandoned.

FIELD OF THE INVENTION

The present invention relates to vasoactive amine binding molecules (VABMs) and their use in the regulation of the action of vasoactive amines. The invention in particular relates to VABMs which are derived from parasite proteins or derivatives thereof. The present invention also relates to the detection and quantification of vasoactive amines and to the control of diseases and injury caused by parasites in animals and humans, especially those caused by ectoparasites of domestic animals. It further relates to the use of vasoactive binding molecules in the treatment of diseases and allergies. The present invention also relates to the use of recombinant DNA technology to produce VABMs.

BACKGROUND

Vasoactive amines such as histamine and serotonin are mediators of inflammation and regulators of certain physiological processes in animals, including humans. Histamine is present in the secretory granules of mast cells and basophils and is,formed by decarboxylation of histidine. It is also present in ergot and plants and may be synthesised synthetically from histidine or citric acid.

The main actions of histamine in humans are stimulation of gastric secretion, contraction of most smooth muscle, cardiac stimulation, vasodilation and increased vascular permeability. In addition to its regulatory role in immune reactions and inflammatory processes, histamine also modulates the production of many cytokines in the body (including those that regulate inflammation) and can interfere with the expression of cytokine receptors. Furthermore, histamine promotes wound healing.

The main pathophysiological roles of histamine are as a stimulant of gastric acid secretion and as a mediator of type I hypersensitivity reactions such as urticaria and hay fever. Histamine or its receptors may also be involved either directly or indirectly in autoimmune disease, e.g. arthritis, and in tumour growth (Falus (1994) *Histamine and Inflammation*, R. G. Landes Co., Austin; pp.139).

Histamine produces its actions by an effect on specific histamine receptors which are of three main types, $H_1$, $H_2$ and $H_3$, distinguished by means of selective antagonist and agonist drugs. Histamine $H_1$ and $H_2$ receptor antagonists have clinical uses but at present histamine $H_3$ receptor antagonists are used mainly as research tools.

$H_1$ receptor antagonists (antihistamines) are widely used for treating allergic reactions including allergic rhinitis (hayfever), urticaria, insect bites and drug hypersensitivities. Drugs that lack sedative or muscarinic-receptor antagonist activities are preferred. $H_1$ receptor antagonists are also used as anti-emetics for the prevention of motion sickness or other causes of nausea including severe morning sickness. Muscarinic-receptor antagonist actions of some antihistamines probably contribute to efficacy but also cause side effects. Some $H_1$ receptor antagonists are fairly strong sedatives and may be used for this action.

There are numerous undesirable effects of $H_1$ receptor antagonists. When used for purely antihistamine actions, all the CNS effects are unwanted. When used for their sedative or anti-emetic actions, some of the CNS effects such as dizziness, tinnitus and fatigue are unwanted. Excessive doses can cause excitation and may produce convulsions in children. The peripheral antimuscarinic actions are always undesirable. The commonest of these is dryness of the mouth, but blurred vision, constipation and retention of urine can also occur. Unwanted effects not related to the drugs' pharmacological actions are also seen. Thus gastrointestinal disturbances are fairly common while allergic dermatitis can follow topical application of these drugs.

$H_2$ receptor antagonists are frequently used as inhibitors of gastric acid secretion. They are used as the drugs of choice in the treatment of peptic ulcer, as second line drugs in the treatment of Zollinger-Ellison syndrome and for treating reflux oesophagitis. Unwanted effects have been reported that include diarrhoea, dizziness, muscle pains, transient rashes and hyper-gastrinaemia. Some $H_2$ receptor antagonists can cause gynaecomastia in men and confusion in the elderly.

Besides these unwanted side effects, some histamine antagonists are troublesome if taken with alcohol or with drugs. For example, the antihistamine Seldane used in combination with antibiotics and antifungals may cause life-threatening side effects.

Drugs used to control the actions of histamine are not always effective. The reasons why they may have limited efficacy may relate to the specificity of these drugs for only a subclass of histamine-receptors, particularly when certain conditions require interference with a larger spectrum of receptors. Histamine binding molecules (HBMs) would compete for histamine binding with all receptors and may thus be more suited for treating certain conditions.

The hormone serotonin (also known as 5-hydroxytryptamine) is both a vasoconstrictor and a neurotransmitter. It can also increase vascular permeability, induce dilation of capillaries and cause the contraction of nonvascular smooth muscle. Serotonin is present in the brain and intestinal tissues and is produced by the pineal gland and by blood platelets. Pathological aspects related to serotonin include abnormal blood pressure, migraine, psychological disorders, respiratory disease and coronary heart disease. Serotonin agonists and antagonists are used to treat some of these disorders, but again often have undesirable side-effects.

There is thus a great need for effective antagonists of vasoactive amines that do not generate the side-effects that detract from their applicability to the treatment of human and animal disorders.

There is also a need for the quantification of histamine in, for example, food products, various body fluids (e.g. plasma or urine) or cell culture supernatants to monitor the effects of certain allergens, for example, or to point to a specific antagonistic therapy for an allergic reaction. Currently used systems (radioimmunoassays and ELISAs) utilize antibodies against histamine or against histamine-derivatives. However, histamine is not very immunogenic, making it hard to raise high-affinity antibodies against it, and most of the quantitation systems used today are not very sensitive or require modification of the histamine to be measured (for example by acylation or methylation).

BRIEF SUMMARY OF THE INVENTION

The use of HBMs to replace antibodies in assays like these would provide a highly sensitive system to measure unmodified histamine. Another advantage of HBMs over anti-histamine antibodies is that they can be used as research tools for the removal of free (unbound) histamine from, for example, cell cultures when studying certain biological processes. Due to the presence of antibody receptors on most cells, antibodies might interfere with the normal functioning of these cells.

It is known that blood-feeding ectoparasites, such as ticks, produce numerous bioactive proteins that immunomodulate the host response to parasite feeding and thereby promote parasite blood-feeding. Such immunomodulatory proteins include immunoglobulin-binding proteins (IGBPs) that are produced in the haemolymph and saliva of ticks and bind to vertebrate host immunoglobulins (Wang and Nuttall (1995) Parasite Immunology 17:517–514). They also include salivary nitric oxide-carrying haeme protein (nitrophorin) of the triatome bug *Rhodnius prolixus*, which, in addition to carrying nitric oxide, can also bind histamine (Ribeiro and Walker (1994) J. Exp. Med. 180:2251–2257). Immunomodulatory proteins are also produced by other blood-feeding parasites, such as mosquitoes and leeches, and venom-producing animals such as snakes and spiders.

We have found that blood-feeding ectoparasites, for example ticks, produce proteins capable of binding to vasoactive amines, particularly histamine and serotonin. These proteins are hereafter referred to as vasoactive amine binding proteins (VABPs).

We have isolated from ticks four VABPs which are named herein as MS-HBP1, FS-HBP1, FS-HBP2 and D.RET6 and which are closely related to each other. These proteins are entirely novel and show no significant similarity to any previously described protein. The DNA sequences encoding these proteins or fragments thereof can be used to isolate other related proteins in the same family from the same or different species.

The present invention provides a vasoactive amine binding protein (VABP) that specifically binds to vasoactive amines with a dissociation constant of less than $10^{-7}$M and which belongs to the same protein family as MS-HBP1, PS-HBP1, FS-HBP2 and D.RET6.

A protein is considered to belong to this family if 40% or more of the amino acids that are completely conserved as identical residues in the alignment of the four VABPs alone, are still completely conserved as identical residues if the protein is included in the alignment, the alignments being obtained using GCG's pileup command (Program manual for the Wisconsin package, 1994; gap creating penalty=2.50; gap extension penalty=0.05). Also included as a member of the VABP family are those proteins from haematophagous arthropods that bind histamine with an affinity characterised by a dissociation constant less than $10^{-7}$M and contain the sequence motifs D/E A W K/R (SEQ ID NO:23) and Y/C E/D L/I W (SEQ ID NO:24).

The VABPs of the present invention include natural biological variants (e.g. allelic variants or geographical variations within the species from which the VABPs are derived).

The present invention also includes functionally-equivalent derivatives and fragments of the vasoactive amine binding proteins, or of proteins belonging to the same protein family as the VABPs. The VABPs, derivatives and fragments of the present invention are hereafter referred to as vasoactive amine binding molecules (VABMs).

BRIEF DESCRIPTION OF THE FIGURES

FIG. 1 is the sequence of FS-HBP1, showing sequencing primers and the sequencing strategy used (SEQ ID NO:15 and 16).

FIG. 2 is the sequence of FS-HBP2, showing sequencing primers and the sequencing strategy used (SEQ ID NO:17 and 18).

FIG. 3 is the sequence of MS-HBP1, showing sequencing primers and the sequencing strategy used (SEQ ID NO:19 and 20).

FIG. 4 is the sequence of D.RET6, showing sequencing primers and the sequencing strategy used (SEQ ID NO:21 and 22).

FIG. 6 shows an alignment of the four cDNA-inferred amino acid sequences of the VABPs, created using the pileup and prettyplot commands of the GCG Wisconsin package (SEQ ID NOs:16, 18, 20, 22).

FIG. 8 is a western blot of salivary gland extracts taken from female and male ticks.

FIG. 10 is a graph depicting contraction-inhibition experiments performed on guinea pig ileum. Abbreviations used: H=histamine (1.25 nmol); wash=Krebs solution. About 2 nmol of FS-HBP2 was added; about 4 nmol (monomer amount) of MS-HBP1 was used.

DETAILED DESCRIPTION OF THE INVENTION

Figure 7:
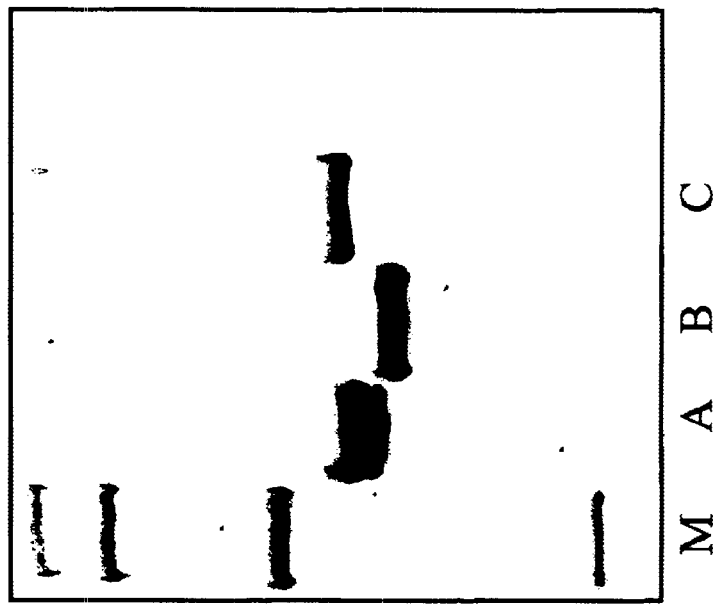
FIG. 7 is a Coomassie-stained 12% SDS-PAGE gel showing recombinantly-produced VABPs. Lane A, rMS-HBP1; lane B, rFS-HBP2; lane C, rFS-HBP1. Molecular weight markers, from top to bottom, indicate 66, 48.5, 29, 18.4 and 14.2kDa.

The VABPs according to the invention are strong and specific vasoactive amine binders with dissociation constant values considerably lower than $10^{-7}$M. Previously described high affinity histamine or serotonin receptors are proteins that form part of the membranes of the cells that are targeted by histamine or serotonin (Falus (1994) supra). They thus differ from the non-membrane bound proteins of the present invention.

The VABPs of the present invention are unrelated to the known immunomodulatory proteins discussed above and have a different method of action. The VABPs of the present invention are secreted from a foreign organism into a mammalian host animal and function as regulators of the host's inflammatory and immune responses. In the case of blood-feeding ectoparasites, such inflammatory and immune responses would otherwise inhibit parasite blood-feeding. This function derives from the ability of the VABPs to bind specifically to vasoactive amines.

The VABPs of the present invention may be derived from blood-feeding parasites and venom-producing animals such as venomous snakes and spiders. Preferably, the VABPs of the present invention are derived from blood-feeding ectoparasites. Most preferably, they are derived from ticks.

As stated above, the invention also includes functionally equivalent derivatives and fragments of the VABPs. 'Functionally equivalent' is used herein to indicate that the derivatives and fragments retain the capacity to bind vasoactive amines or that they contain epitopes which can be used in the development of vaccines that target members of the VABP protein family as defined above. The derivatives and fragments may be derived from native VABPs by single or multiple amino-acid substitution(s), addition(s), insertion(s) and/or deletion(s) or by chemical modification of one or more of the amino-acids, for instance by deglycosylation of glycosylated forms.

For instance, a derivative may include an additional protein or polypeptide fused to the VABP at its amino- or carboxy-terminus or added internally to the VABP. The purpose of the additional polypeptide may be to aid detection, expression, separation or purification of the VABM or may be to lend additional properties to the VABPs as desired. Examples of potential fusion partners include β-galactosidase, glutathione-S-transferase, luciferase, polyhistidine tags, T7 polymerase fragments and secretion signal peptides.

The VABMs of the present invention can be prepared using known techniques of molecular biology and protein chemistry. For example, the VABMs may be prepared by chemical peptide synthesis. This technique is especially useful for the generation of short peptides derived from the VABPs for use as immunogens. The VABMs may also be prepared using the known techniques of genetic engineering such as site-directed or random mutagenesis as described, for example, by Sambrook et al., 1989. The VABMs may also be synthetically prepared, using organic chemistry techniques, resulting in molecules structurally and functionally mimicking the histamine-binding site of any of the members of the VABP family.

VABMs of the present invention may be prepared in recombinant form by expression in a host cell. Such expression methods are well known to those of skill in the art and many are described in detail by Sambrook et al. (1989) *Molecular Cloning: A Laboratory Manual*, Cold Spring Harbor). A suitable expression vector can be chosen for the host of choice. The vector may contain a recombinant DNA molecule encoding a VABM operatively linked to an expression control sequence that is recognised by the host transcription machinery.

Suitable hosts include commonly used prokaryotic species, such as *E. coli*, or eukaryotic yeasts that can be made to express high levels of recombinant proteins and that can easily be grown in large quantities. Cell lines grown in vitro are also suitable, particularly when using virus-driven expression systems such as the Baculovirus expression system which involves the use of insect cells as hosts. VABMs may also be expressed in vivo, for example in insect larvae or in mammalian tissues.

According to a yet further aspect, the present invention provides for use of such VABMs to bind histamine in mammals, thereby to regulate its action and to control its pathological effects.

The present invention also includes the use of the VABMs of the present invention as anti-inflammatory agents. Preferably, the VABMs are provided as a pharmaceutical composition including an inert carrier or carriers. The VABM may constitute the sole active component of the composition or can form part of a therapeutic package, such as a component of creams for topical administration to insect, snake or scorpion bites, or to skin affected by dermatitis. The proteins may also be used as carrier molecules for histamine and histamine-related compounds, in creams, oils, powders or pills, to provide slow release of the bound components.

The present invention also comprises the use of the VABMs of the present invention for the quantification of histamine levels (for example, in blood, nasal lavage fluid, tissues or food products). The VABMs may be supplied as part of a kit together with means of detection that allow the accurate quantification of the histamine in the sample to be tested (for example radiolabelled histamine, anti-VABM-antibodies or enzymes such as alkaline phosphatases, peroxidases or luciferases). Such kits will resemble radioimmunoassay, scintillation proximity assay, or ELISA kits, with the VABMs as binding molecules in place of antibodies directed against histamine or against histamine analogues. One aspect of the present invention comprises such kits incorporating the VABMs of the present invention.

The VABMs of the present invention can also be used for the detection of vasoactive amines. Any technique common to the art may be used in such a detection method and may comprise the use of blotting techniques (Towbin et al. (1979) Proc. Natl. Acad. Sci. USA 76:4350–5354), gel retardation or affinity chromatography. The entire VABP may be used, or simply an active binding fragment in order to detect substrate. In another embodiment, the VABP may be fused either genetically or synthetically to another protein such as alkaline phosphatase, luciferase or peroxidase in order to facilitate detection.

The invention also comprises the use of the VABMs of the present invention as histamine-binding entities bound to a support that can be used to remove, isolate or extract histamine (from body tissues, blood or food products). The support may comprise any suitably inert material such as gels, magnetic and other beads, microspheres, binding columns and resins.

The present invention also includes the use of VABMs as tools in the study of inflammation, inflammation-related processes or other physiological effects of vasoactive amines such as the role of histamine in the formation of gastric ulcers or its role in immune reactions. For example, the VABMs may be used for histamine or serotonin depletion in cell cultures or in inflamed animal tissues in order to study the importance of histamine or serotonin in these systems.

Metazoan parasites, particularly arthropods and helminths, are also sources of infectious diseases and other injurious effects that have major impacts in human and veterinary medicine. Control of arthropod and helminth parasites currently relies primarily on the use of chemicals such as acaricides and antihelmintics. Attempts have been made to use immunological means of control through the use of vaccine technology. There has been some success in identifying certain protective antigens as potential vaccine candidates, but only a few have as yet come to commercial fruition, most notably for the cattle lungworm *Dictyocaulus viviparous* and the cattle tick *Boophilus microplus*. Despite these developments, there is nonetheless a continuing need for metazoan parasite vaccines and in particular for a vaccine which may be used across a broad range of arthropod and/or helminth genera.

The present invention therefore also provides for the use of the VABMs as defined above as immunogens for use as metazoan parasite vaccines and in particular as protective immunogens in the control of diseases caused by arthropod and other metazoan parasites. Suitable candidates for vaccination include domesticated animals such as cattle, goats, sheep, dogs, cats and other animals which require protection against metazoan parasites, especially ticks. The vaccine may include adjuvants of the type which are well known in the art.

Nucleic acid molecules comprising a nucleotide sequence encoding a VABM of the invention form further aspects of the invention. These molecules include DNA, cDNA and RNA, as well as synthetic nucleic acid species.

The cDNAs encoding the four particular VABPs are disclosed herein by way of example and their amino acid sequences are shown in FIGS. 1 to 4 (nucleotides (SEQ ID NO:15, 17, 19, 21) and amino acids (SEQ ID NO:16, 18, 20, 22) are given in their standard one letter abbreviations).

The preferred nucleic acid molecule, according to the invention, comprises a nucleotide sequence identical to or complementary to any one of, or any VABM-encoding portion of, any one of the nucleotide sequences shown in FIGS. 1 to 4 and 6, or a sequence which is degenerate or substantially homologous therewith, or which hybridises with the said sequence. By 'substantially homologous' is meant sequences displaying at least 60% sequence homology. The nucleic acid sequences according to the invention may be single- or double-stranded DNA, cDNA or RNA. Preferably, the nucleic acid sequences comprise DNA.

'Hybridising sequences' included within the scope of the invention are those binding under non-stringent conditions (6×SSC/50% formamide at room temperature) and washed under conditions of low stringency (2×SSC, room temperature, or 2×SSC, 42° C.) or conditions of higher stringency, e.g. 2×SSC, 65° C. (where SSC=0.15M NaCl, 0.015M sodium citrate, pH 7.2).

The invention also includes cloning and expression vectors containing the DNA sequences of the invention. Such expression vectors will incorporate the appropriate transcriptional and translational control sequences, for example enhancer elements, promoter-operator regions, termination stop sequences, mRNA stability sequences, start and stop codons or ribosomal binding sites, linked in frame with the nucleic acid molecules of the invention.

Additionally, it may be convenient to cause the recombinant protein to be secreted from certain hosts. Accordingly, further components of such vectors may include nucleic acid sequences encoding secretion signalling and processing sequences.

Vectors according to the invention include plasmids and viruses (including both bacteriophage and eukaryotic viruses). Many such vectors and expression systems are well known and documented in the art. Particularly suitable viral vectors include baculovirus-, adenovirus- and vaccinia virus-based vectors.

A variety of techniques are known and may be used to introduce the vectors according to the present invention into prokaryotic or eukaryotic cells. Suitable transformation or transfection techniques are well described in the literature (Sambrook et al. (1989) supra). In eukaryotic cells, expression systems may either be transient (e.g. episomal) or permanent (chromosomal integration) according to the needs of the system.

Nucleic acid molecules according to the present invention may also be used to create transgenic animals. This may be done locally by modification of somatic cells or by germ line therapy to incorporate heritable modifications.

The invention therefore also includes transformed or transfected prokaryotic or eukaryotic host cells or transgenic organisms containing a nucleic acid molecule according to the invention as defined above.

A further aspect of the invention provides a method for preparing a VABM of the invention which comprises culturing a host cell containing a nucleic acid molecule according to the invention under conditions whereby said protein is expressed and recovering said protein thus produced.

Various aspects and embodiments of the present invention will now be described in more detail by way of example, with particular reference to VABPs isolated from ticks, and especially the tick *Rhipicephalus appendiculatus*. It will be appreciated that modification of detail may be made without departing from the scope of the invention. All documents mentioned in the text are incorporated herein by reference.

EXAMPLES

Ticks. Ticks were reared according to Jones et al., (1988) Animal Technology 39:99–106). All three developmental stages of *Rhipicephalus appendiculatus* and *Dermacenter reticularis* and were fed on Dunkin Hartley guinea pigs except adult *Dermacenter reticularis* which were fed on rabbits. When not feeding, all ticks were maintained at 21° C. and 85–90% relative humidity.

Example 1

Identification of Proteins

Salivary glands were excised from female adult *R. appendiculatus* specimens that had been feeding on guinea pigs for three days. Male ticks were fed for four days. Glands were homogenised in phosphate-buffered saline (PBS; pH7.4), cellular debris was removed by centrifugation for 3 minutes at 10,000 g and the supernatant was then applied to a column containing 400 ml histamine-agarose suspension (Sigma). Unbound protein was washed out of the column with 10 ml PBS containing 5% glycerol and bound protein could then be eluted using 100 mM histamine in PBS (2 ml). The eluans were concentrated using a centricon 3 ultrafiltration unit (Amicon).

Figure 5:
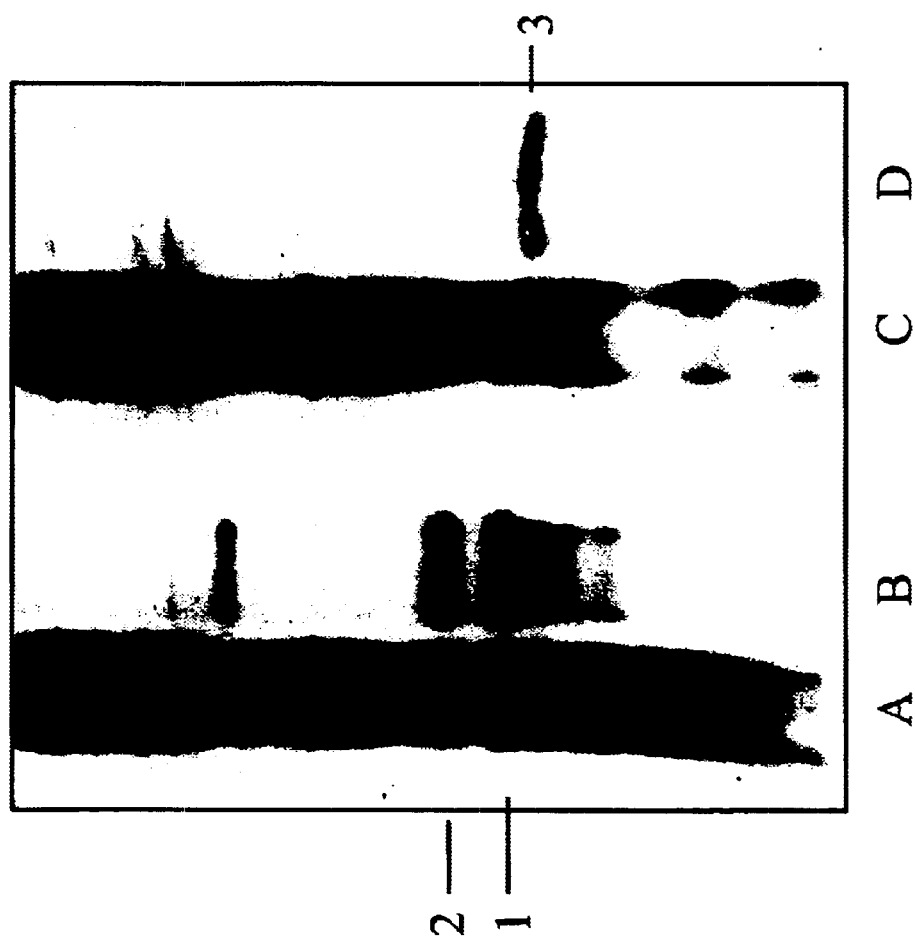
FIG. 5 is a Coomassie-stained 12% SDS-PAGE gel showing salivary gland extracts from ticks that have been purified on a histamine-binding column. Salivary gland extract of female ticks before (lane A) and after purification (lane B; 1=FS-HBP1, 2=FS-HBP2); salivary gland extract of male ticks before (lane C) and after purification (lane D; 3=MS-HBP1). Molecular weight markers are indicated.

The extracts were run on a 12% SDS-PAGE gel, identifying two major proteins from female ticks and one from male ticks (see FIG. 5). These proteins were termed female-specific histamine binding proteins 1 and 2 (FS-HBP1 and FS-HBP2) and male-specific histamine binding protein 1 (MS-HBP1). MS-HBP1 was never detected in female tissues, but was clearly present in the salivary glands of males and nymphs and in whole body homogenates of larvae.

Example 2

Cloning of Genes cDNA library construction. In order to clone the cDNAs encoding the three proteins of example 1, a cDNA library was constructed. Salivary glands were excised from 20 male and 20 female adult *R. appendiculatus* specimens that had been feeding on guinea pigs for two days. The glands were collected in an Eppendorf tube in dry ice. Messenger RNA was isolated using the FastTrack mRNA isolation kit (Invitrogen).

For synthesis of cDNA and its unidirectional insertion into the Lambda Zap II vector, the Zap cDNA synthesis kit (Stratagene) was used. Prior to insertion into the lambda vector, the cDNA was fractionated over a Sephacryl S400 (Pharmacia) column. A DNA library (termed d2-I) was constructed using low molecular weight cDNAs (ranging from approximately 100 to 2,000 base pairs). The higher molecular weight fraction was used to construct a second library (d2-II). Packaging utilised Packagene (Promega) packaging extracts in accordance with the manufacturer's instructions. Approximately $1.5 \times 10^6$ plaque-forming units (PFU) of each library were amplified in XL-1 Blue cells (Stratagene).

A *Dermacenter reticularis* library was constructed with salivary gland mRNA from adult females that had fed on rabbits for 3 days. Isolation of mRNA, and cDNA library construction was as described above for the d2-II library, except that the Zap Express (predigested vector) Cloning kit (Stratagene) was used instead of the Lambda Zap II kit.

Screening of the d2-II cDNA library. Phagemids were excised in vivo from a fraction of the library and used to generate double-stranded pBluescript SK(−) plasmids in XL1-Blue cells (Stratagene), as described by Short et al., (1988) Nucl. Acids Res. 16:7583–7600). Colonies were plated out on ampicillin-containing LB agar plates supplemented with 5-bromo4-chloro-3-indolyl-β-D-galactopyranoside (X-Gal, Melford Laboratories, UK) and isopropyl-β-D-thiogalactopyranoside (IPTG, Novabiochem) for blue/white colony selection. About 75 plasmids from white colonies were selected for sequencing. The size of the DNA inserts ranged from 250 to 1000 base pairs as determined by digestion with PvuII and electrophoresis over a 1% agarose gel.

Clones FS-HBP1, FS-HBP2 and MS-HBP1 were obtained and partially sequenced. The d2-II library was then screened for additional clones by DNA hybridisation of plaque lifts (Sambrook et al. (1989) supra) with digoxygenin-labelled probes (Boehringer Mannheim). The probes were constructed by random primer labelling using the purified insert from the original clones and detected using anti-digoxygenin antiserum conjugated with alkaline-phosphatase (Boehringer Mannheim). For each original clone, 3 additional clones were isolated and sequenced.

Screening of the Dermacenter reticularis cDNA library. Firstly, a DNA probe was constructed. A fraction of the Dermacenter library was not inserted into the Zap Express vector, but instead was submitted to PCR, using the degenerate primers 5′-AAYGGNGARCAYCARGAYGCNTGGAA (SEQ ID NO:1) (forward) and 5′-KTRTMRTCNGTNRYCCANARYTCRTA (reverse) (SEQ ID NO:2). These primers were based on conserved domains in the FS-HBP1, FS-HBP2 and MS-HBP1 cDNAs and proteins.

The PCR consisted of 35 cycles with a 30-second melting step at 95° C., a 30-second primer-annealing step at 50° C. and a 30-second extension step at 72° C. (Taq polymerase was from Perkin Elmer, deoxynucleotides were from Pharmacia). A single DNA band of the expected size (around 400 base pairs) was obtained, which was labelled with digoxygenin to screen the library (as above). D.RET6 was one of several positive clones.

Sequencing. The entire coding and non-coding strands of the FS-HBP1, FS-HBP2, MS-HBP1 and D.RET6 inserts were sequenced. Plasmids were purified from overnight cultures according to Goode and Feinstein (1992) BioTechniques 12:374–375), alkali-denatured (Mierendorf and Pfeffer (1987) Methods Enzymol. 152:556–562) and sequenced by means of the Sanger dideoxy-mediated chain termination reaction (Sanger and Coulson (1975) J. Mol. Biol. 94:441–448). The sequencing strategies are shown in FIGS. 1–4.

FS-HBP1. As shown in FIG. 1, the original clone was sequenced from the T3 (forward) and T7 (reverse) primer sites flanking the pBluescript SK(−) polylinker region. Additionally, subclones XVIIIa (comprising nucleotides 221 to 770 of the original insert) and XVIIIb (nucleotides 509 to 770) were sequenced from the T3 site (reactions indicated by T3a and T3b in the figure). Subclones XVIIIc (1 to 221) and XVIIId (1 to 509) were sequenced from the T7 site (T7c and T7d).

Xviiia was created by digestion of the original clone with PstI (cuts at position 221 of the insert and in the upstream polylinker region) followed by religation; Xviiib by digestion with XbaI (cuts at position 509 and upstream of the insert). Xviiic and Xviiid were obtained using EcoRI (cuts upstream of the insert) together with PstI and XbaI, respectively and ligating the excised pieces back into pBluescript (SK−) plasmid. The signal sequence is given in bold lettertype in the figure and the signal cleavage site is indicated by the vertical arrow ( ). The underlined sequence was also obtained by amino terminal sequencing of the expressed protein.

F8-HBP2. FIG. 2 shows the cDNA (SEQ ID NO:17) and inferred amino acid sequence (SEQ ID NO:18)of the clone FS-HBP2. The original clone was sequenced from the T3 (forward) and T7 (reverse) primer sites, as were 2 subclones (52a and 52b) obtained by digestion of 52-1 with HincII (cuts at position 254, the reactions are indicated by T3b and T7a). HincII was used in combination with XhoI (cuts the polylinker downstream of the insert) for construction of 52a (comprising nucleotides 1 to 254) and in combination with SmaI (cuts upstream) for construction of 52b (nucleotides 254 to 793). Digestion was followed by bluntending with T4 polymerase (New England Biolabs) and religation of the plasmids. Finally, we used forward (→) and reverse (←), insert-specific primers that were identical or complementary to the underlined sequences in the figure.

The polyA tail is in italic, the putative polyadenylation signal is doubly underlined. The signal sequence is given in bold lettertype, the signal cleavage is indicated by the vertical arrow ( ). The underlined sequence was also obtained by amino terminal sequencing of the expressed protein.

Ms-HBP1. FIG. 3 shows the cDNA (SEQ ID NO:19) and inferred amino acid sequence (SEQ ID NO:20) of clone MS-HBP1. The clone was sequenced from the T3 (forward) and T7 (reverse) primer sites flanking the pBluescript SK(−) polylinker region. Additionally, we used forward (→) and reverse (←), insert-specific that were identical or complementary to the underlined sequences in the figure.

The triple line indicates the putative N-glycosylation site. Italics denote the polyA tail and the double line marks the putative polyadenylation signal. The signal sequence is given in bold lettertype, the signal cleavage is indicated by the vertical arrow ( ). The underlined sequence was also obtained by amino terminal sequencing of the expressed protein.

D.RET6. The cDNA and inferred amino acid sequence of clone D.RET6 is given in FIG. 4 (SEQ ID NO:21 and 22). The DNA insert was sequenced from the T3 (forward) and T7 (reverse) primer sites flanking the pBK-CMV polylinker region and from the forward (→) and reverse (←), insert-specific primers that were respectively identical or complementary to the underlined sequences in the figure. The putative signal sequence is given in bold lettertype, the signal cleavage is indicated by the vertical arrow ( ).

Sequence analysis. Sequence data were analyzed using the GCG sequence analysis software (Program Manual for the Wisconsin Package, 1994). Protein database searches were performed at the National Centre for Biotechnology Information (NCBI) using the BLAST network service.

Figure 6:
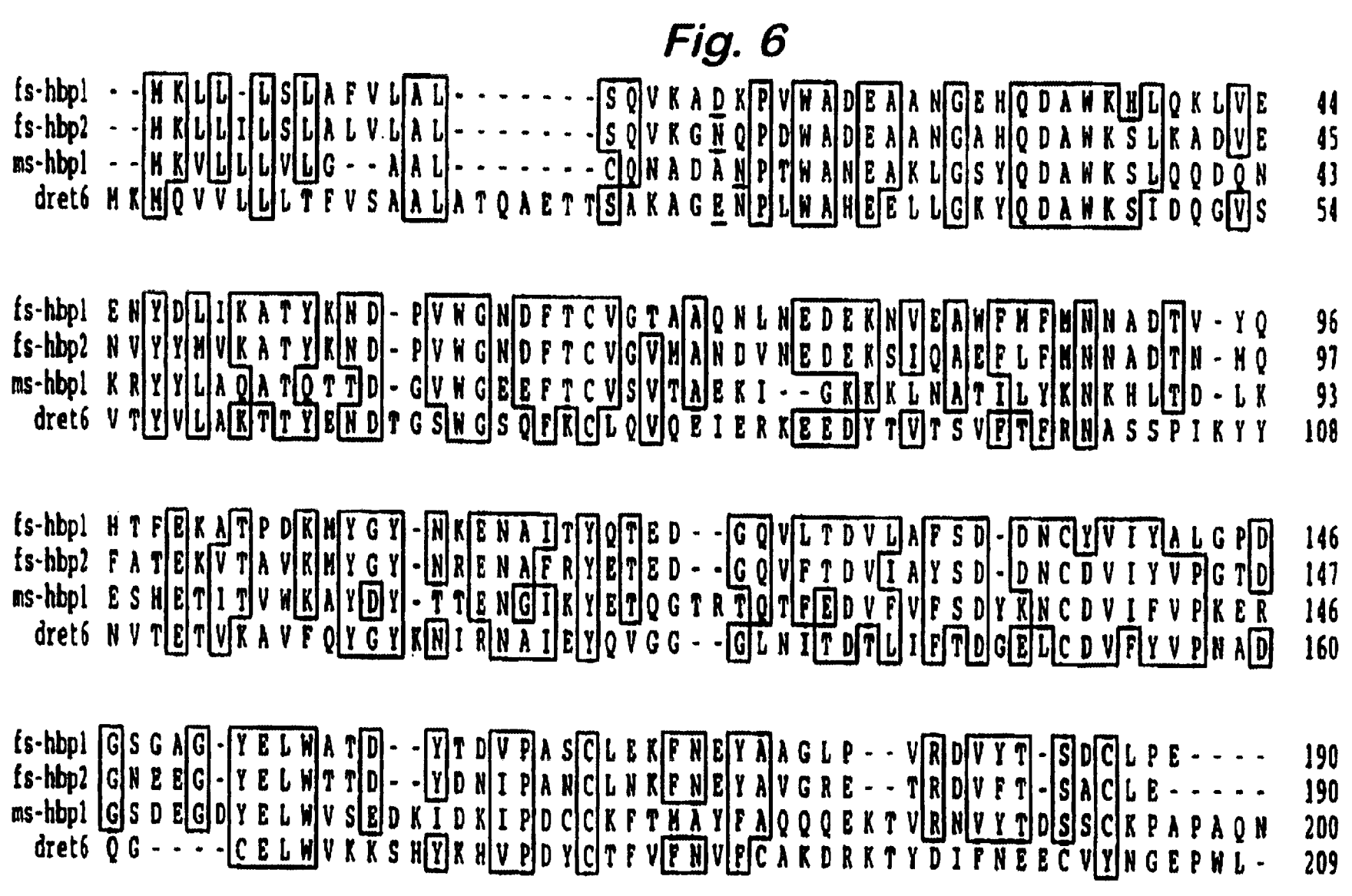

An alignment of the cDNA-inferred amino acid sequences of the VABPs is shown in FIG. 6. This was created using the pileup and prettyplot commands of the GCG software. The mature proteins begin at the underlined amino acids, as determined by N-terminal sequencing of the secreted VABPs (see below), suggesting that the preceding regions represent signal sequences. The calculated molecular weights, excluding signal sequences are 19 442 for FS-HBP1, 19 471 for FS-HBP2, 21 026 for MS-HBP1 and 21 025 for D.RET6. Calculated isoelectric points are 4.0, 3.9, 5.0 and 4.6 respectively.

MS-HBP1 has 40% identity (57% similarity) with FS-HBP1, 43% (62%) with FS-HBP2 and 32% (50%) with D.RET6. FS-HBP1 has 66% identity (78% similarity) with FS-HBP2 and 32% (49%) with D.RET6. FS-HBP2 has 39% identity and 56% similarity with D.RET6. These percentages were obtained with the Bestfit command of the GCG software, using gap weight of 3 and length weight of 0.1.

The predicted secondary structures are similar for the four proteins, with α-helices prevailing in the amino terminal half of the molecules and relatively more β-sheet and turns in the carboxy terminal half. The lower affinity of FS-HBP1 for (positively-charged) histamine suggests that residues at these positions may form part of the binding site.

Example 3

Recombinant Protein Expression

Construction of clones. FS-HBP1, FS-HBP2 and MS-HBP1 were expressed as histidine-tagged proteins (rFS-HBP1, rFS-HBP2 and rMS-HBP1) in *Spodoptera frugiperda* ovarian cells (Sf21).

In order to append the $His_6$ tag, the coding region of FS-HBP1 was first amplified using the polymerase chain reaction (PCR). The PCR consisted of 20 cycles with a 30-second melting step at 95° C., a 30-second primer-annealing step at 50° C. and a 30-second extension step at 72° C. The forward primer used was: 5'-GCAGGAGCTCGGCACGAG (SEQ ID NO:3); the reverse primer was: 5'-TTTACTAGTGATGGTGAT GAT-GATGGATCCCTTCTGGGAGGCAATCACTT (SEQ ID NO:4). The primers were designed so that a SacI site was added upstream of the start codon, whilst the stop codon was replaced by a BamHI site, followed by 6 histidine codons and an SpeI site comprising a TAG stop codon. The PCR product was cut with SacI and SpeI. The latter enzyme creates a compatible overhang with XbaI, enabling the fragment to be ligated between the SacI and XbaI sites of the pAcC129.1 transfer vector (Livingstone and Jones (1989) Nucleic Acids Res. 17:2366), generating the plasmid pACC129.1-FS1.HIS. This plasmid therefore contained the sequence Gly-Ile-(His)$_6$ appended to the carboxy terminus of the FS-HBP1 translation product.

This plasmid pACC129.1-FS1.HIS was also used for expression of histidine-tagged FS-HBP2 and MS-HBP1. The FS-HBP1 cDNA was deleted using SacI and BamHI thus leaving the histidine codons intact. An upstream SacI and a downstream BglII site (BglII and BamHI create compatible overhangs) were added to the FS-HBP2 and MS-HBP1 coding regions by PCR. The PCR consisted of 20 cycles with a 30-second melting step at 950° C., a 30-second primer-annealing step at 50° C. and a 30-second extension step at 72° C. The forward primer, in the case of FS-HBP2 was: 5'-AAGGAGCTCAGCATGAAGCTTCTCAT (SEQ ID NO:5); the reverse primer was: 5'-TATAGATCT CTAG-GCMGCACTTGTG (SEQ ID NO:6). In the case of MS-HBP1 the forward primer was: 5'-GCAGGAGCT CGGCACGAG (SEQ ID NO:7), and the reverse primer was: 5'-TATAGATCTGGTTCTGAGCTGGTGCTG (SEQ ID NO:8).

Following PCR, the derived cDNAs were inserted into the vector. A Gln-Ile-(HIS)$_6$ sequence was thus added to the carboxyterminus of the MS-HBP1 translation product, and Ile-(His)$_6$ to the FS-HBP2 translation product.

The baculovirus expression system was used for expression of the three tagged polypeptides. Spodoptera (Sf21) cells were transfected with the transfer vectors and baculovirus (BacPak6; Clontech). Recombinant virus was amplified as according to Kitts and Possee (1993) BioTechniques 14:810–817). The VABPs are clearly secretion products since they are mainly found in the culture medium of transfected cells as well as in saliva.

The coding region of (mature) FS-HBP2 was also cloned into the pET-23a(+) expression vector. The sequences from position (a) to (b) and from (c) to (d) in FIG. 7 were deleted in truncated versions of bacterially-expressed FS-HBP2. The N-terminally truncated protein was obtained by PCR on the pACC129.1-HIS plasmid containing FS-HBP2, using the forward primer 5'-TATGGATCCTTCACT TGCGTGGGTGTT (SEQ ID NO:9)and the reverse primer 5'-TATAGCGGCCGCCCGGGCTAGTGATGGTGAT GATGAT (SEQ ID NO:10). The PCR product was cut with BamHI and NotI and inserted in between the BamHI and NotI sites of the pET-23a(+) vector.

In the case of the carboxyterminal truncation, the complete FS-HBP2 coding region was inserted into the pET23a (+) vector, using-the forward primer: 5'-TATAGGATC CGGGAGCTCCAATCAGCCAGATTGGGC (SEQ ID NO:11) and the reverse primer: 5'-TATAGCGGCCGCCCG GGCTAGTGATGGTGATGATGAT (SEQ ID NO:12). The PCR product was cut with BamHI and NotI and inserted between the BamHI and NotI sites of the pET-23a(+) vector. The plasmid (with insert) was then used as a template for PCR with the inverse primers; 5'-TATATGGTACCCATC ATCATCACCATCAC (SEQ ID NO:13) and 5'-ATATATGGTACCGTTGTCGTAATCCGTAGTC (SEQ ID NO:14). This resulted in amplification of the complete plasmid minus the region to be deleted. Religation was performed after cutting with KpnI (the primers contain KpnI sites). The original, unamplified plasmid was destroyed by digestion with DpnI, prior to transformation. All PCRs consisted of 20 cycles with a 30second melting step at 95° C., a 30-second primer-annealing step at 50° C. and a 90 second extension step at 72° C.

Protein purification and production of antisera. 60 hours after infection of the Sf21 cells, the culture medium was collected, cells and cellular debris were spun down (2,000 g, 10 minutes) and the supernatant was fractionated by $(NH_4)_2SO_4$ precipitation. rFS-HBP1 and rFS-HBP2 precipitated in the 50 to 80% $(NH_4)_2SO_4$ fraction and MS-HBP1-His in the 65–100% fraction. The pellets were washed in 100% $(NH_4)_2SO_4$, redissolved in PBS and purified over Ni-agarose columns (Qiagen) according to Janknecht et al. (1991) Proc. Natl. Acad. Sci. USA 88:8972–8976. The histidine-tagged proteins were eluted using imidazole. Centricon 10 concentrators (Amicon) were used to concentrate the eluants and for buffer exchange. The purified protein was stored at −20° C. in PBS.

For production of polyclonal antisera, purified recombinant protein (ca. 2 μg in 150 μl PBS) was mixed with an equal volume of Montanide ISA 50 adjuvant (Seppic, France) and subcutaneously injected into Dunkin Hartley guinea pigs. This procedure was repeated every 10 days. Serum was collected 10 days after the 4th injection.

Electrophoresis and Western Blotting

Salivary glands (and other tissues) were excised from ticks at different time points of the feeding period, and homogenised in PBS. The homogenates were centrifuged at 10,000 g for 5 minutes and the supernatants were submitted to sodium dodecyl sulphate-polyacrylamide electrophoresis (SDS-PAGE; Laemmli (1970) Nature 277:680–685).

FIG. 7 shows a 12% SDS-PAGE gel over which rFS-HBP1, rFS-HBP2 and rMS-HBP1 were run. rFS-HBP1 and rFS-HBP2 run on agarose with apparent molecular masses of ~21 and ~24kDa respectively, whilst rMS-HBP2 runs at ~22kDa.

For Western blotting, proteins were transferred to nitrocellulose (Gelman Sciences) by means of semi-dry electroblotting (Kyhse-Anderson (1984) J. Biochem. Biophys. Methods 10:203–209) using an AE-6675 Horizblot apparatus (Atto Corporation, Japan). FS-HBP1, FS-HBP2 and MS-HBP1 were identified using the antisera produced in guinea pigs (see above), in combination with goat anti-guinea pig immunoglobulins conjugated to alkaline phosphatase (Sigma). Kinase activity was visualised with nitro blue tetrazolium salt and 5-bromo-4-chloro-3-indolyl phosphate (Blake et al. (1984) Anal. Biochem. 136:175–179).

Eventual asparagine-linked glycosylation of proteins was studied by means of mobility shift assays. SDS-PAGE and immunoblotting were carried out with salivary gland extracts and recombinant protein samples, before and after treatment with N-glycosidase F (PNGase F; New England Biolabs), an endoglycosidase that hydrolyses all common types of Asn-glycan chains from glycoproteins (Maley et al. (1989) Anal. Biochem. 180:195–204). Only MS-HBP1 shows any downward shift in mobility in SDS-PAGE gels upon treatment with N-glycosidase F, indicating that it is a glycoprotein. The downward shift corresponds to a 2–3kDa change in molecular weight.

FIG. 8 shows western blots containing salivary gland extracts of female (A and B) and male (C) ticks taken at different time points of the adult feeding period and resolved over a 12% SDS-PAGE gel. Anti-FS-HBP1 (A) and anti-FS-HBP2 (B) sera show positive reactions from the first to the third day after attachment (p.a.). The anti-MS-HBP1 serum (C) detected MS-HBP1 from the first day p.a. until the end of the feeding period.

N-terminal sequencing. The amino terminal sequences of purified rFS-HBP1, rFS-HBP2 and rMS-HBP1 were determined at the MRC Immunochemistry Unit of the Department of Biochemistry of the University of Oxford. Samples were run on SDS-PAGE gels according to the method of Schagger and von Jagow (1987) Anal. Biochem. 166 and electroblotted onto ProBlott membranes (Applied Biosystems, Warrington, England). The membranes were stained with Coomassie brilliant blue and the bands of interest were excised and sequenced, according to Matsudaira (1987) J. Biol. Chem. 262:10035–10038). Electroblotted samples were run on an Applied Biosystems 494A "Procise" protein sequencer (Perkin-Elmer, Applied Biosystems Division, Warrington, UK) using an Applied Biosystems "Mini Blott" cartridge (onto which the membrane pieces were inserted). The manufacturer's recommended programme for membrane-bound samples was used for sequencing.

Example 4

Characterisation of Proteins

Histamine binding assays. The purified recombinant proteins were submitted to histamine binding assays as set out in Warlow and Bernard (1987) Mo. Immun. 24:27–37). This method uses protein precipitation to separate free from bound ligand (radiolabelled histamine) by addition of polyethylene glycol ($M_w$ 8000) and centrifugation. In all experiments, thin-layer chromatographs were run in an acetate-ammonia solvent system after a four hour incubation period to ensure that no metabolization of histamine had occurred.

Figure 9A:
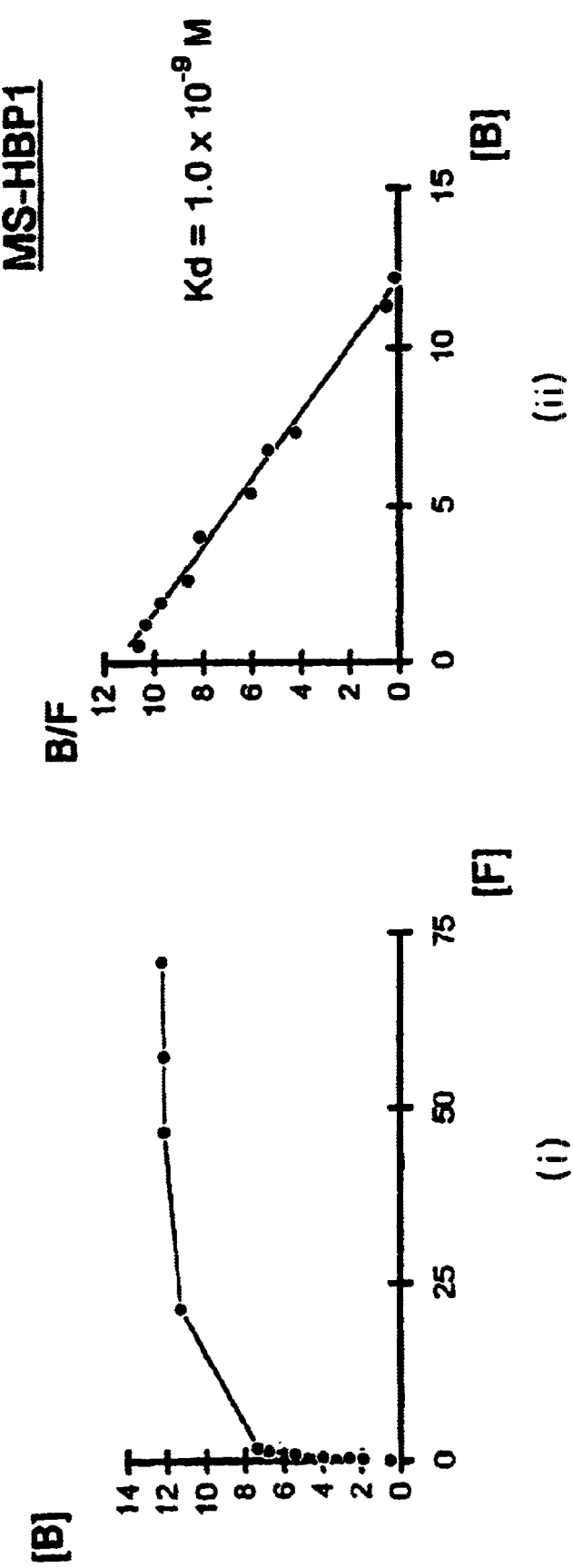
FIG. 9 shows saturation curves and Scatchard plots illustrating the histamine-binding properties of purified VABPs.
Figure 9B:
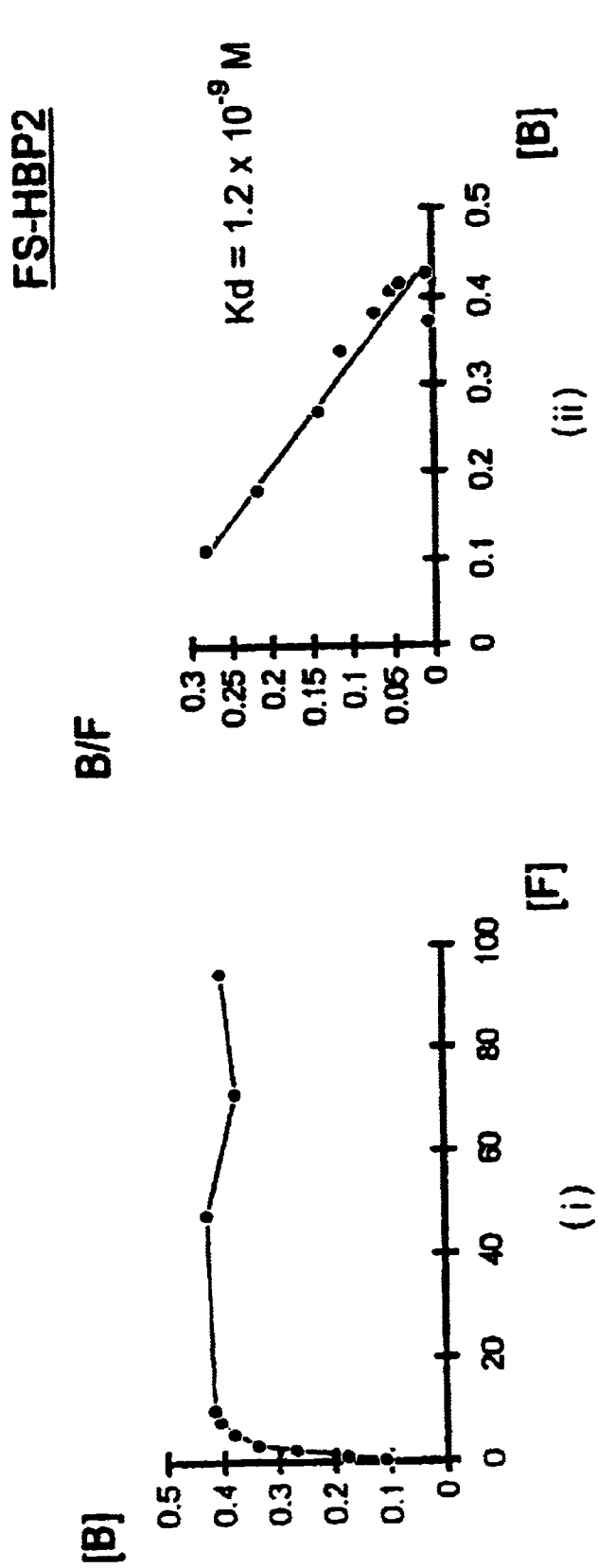

Saturable binding of $^3$H-histamine was obtained with all 3 rVABPs (FIGS. 9Ai, 9Bi and 9Ci). Scatchard plots (FIGS. 9Aii, 9Bii and 9Cii) show high affinities for rMS-HBP ($K_d=1.2\times10^{-9}$M; SD=0.4; 3 measurements) and for rFS-HBP2 ($K_d=1.7\times10^{-9}$M; SD=0.9), but a lower affinity for rFS-HBP1 ($K_d=7.8\times10^{-8}$M; SD=1.5), suggesting that binding histamine may not be the primary function of this protein.

There is some evidence for co-operative binding in the case of rMS-HBP1. When samples containing $^3$H-histamine (~0.3 pmol; 11,200 cpm) and excess amounts of rMS-HBP1 (~100 pmol) were supplemented with small amounts of histamine (0.5 pmol), a significant increase of bound radioligand was measured (7,560±110 cpm, compared to 6,840±150 cpm; 5 measurements), indicating an enhanced binding capacity. Co-operative binding is in agreement with the dimer or polymer nature of MS-HBP1. Indeed, MS-HBP1 appears to form intermolecular disulphide bridges; it has a lower mobility on SDS gels when reducing agent is left out of the loading buffer. The FS-HBPs seem to have only intramolecular disulphide bonds, as is suggested by the higher mobilities in the absence of reducing agent.

In a competition experiment (carried out in triplicate), a series of histamine-like compounds [histamine, imidazole, serotonin, dopamine, the H1-receptor agonist betahistine, the $H_1$ antagonists chlorpheniramine and pyrilamine, the H2 agonist dimaprit, and the H2 antagonists ranitidine and cimetidine] were added to each of the rVABPs in 1000-fold the amounts at which cold histamine displaces more than 95% of $^3$H-histamine from the binding sites. The histamine-like compounds caused little or no displacement of radioligand, indicating that the VABPs bind histamine specifically and in a different manner from the H1 and H2 receptors.

FS-HBP2 was expressed in the pET-23a(+) vector in AD494(DE3)pLysS bacteria (Novagen). Bacterially-expressed FS-HBP2 binds histamine with a somewhat lower affinity ($K_d=0.6-0.9\times10^{-8}$M) than that expressed in the baculoviral system. Truncated versions of the protein (see above) that lack either the 45 N-terminal amino acids or the 28 C-terminal amino acids do not bind to histamine at all. This suggests that the overall structure of FS-HBP2 is important for histamine binding and that the binding site is more likely to be determined by dispersed residues, rather than a stretch of consecutive amino acids located somewhere on an α-helix or β-sheet.

Contraction-inhibition. Contraction-inhibition experiments (FIG. 10) were carried out on guinea pig ileum suspended in a 10 ml chamber containing aerated Krebs solution. Contractions (recorded as peaks) were induced by adding 1.25 nmol histamine (H) to the chamber. After a peak was reached histamine was washed away with Krebs solution (W), allowing the ileum to relax.

Contraction was substantially reduced by adding ~2 nmol rFS-HBP2 (F2) together with the histamine. ~2 nmol of rFS-HBP1 had no significant effect (data not shown). ~4 nmol (monomer amount) of rMS-HBP1 (M) added together with histamine completely inhibited contraction, even after extra histamine (xH) was added.

The rMS-HBP1 and rFS-HBP2 proteins are strong enough binders to compete with histamine with the H1 receptors of guinea pig ileum (see FIG. 10). In accordance with its relatively low affinity, little or no inhibition of ileum contraction was observed with rFS-HBP1.

What is claimed is:

1. A vasoactive amine binding protein (VABP) that binds to vasoactive amines with a dissociation constant of less than $10^{-7}$ M, has a sequence homology to the VABP clones male specific histamine binding protein 1 (MS-HBP1) (SEQ ID NO:20), female specific histamine binding protein 1 (FS-HBP1) (SEQ ID NO: 16), female specific histamine binding protein 2 (FS-HBP2) (SEQ ID NO: 18), and Dermacenter reticularis 6 (D.RET6) (SEQ ID NO: 22), such that 40% or more of the amino acids of said VABP clones that are completely conserved as identical residues when said VABP clones are in alignment with each other, are still completely conserved when said VABP is included in said alignment; and that contains a sequence motif selected from the group consisting of the motifs (Asp or Glu)-Ala-Trp-(Lys or Arg) (SEQ ID NO: 23) and (Tyr or Cys)-(Glu or Asp)-(Leu or Ile)-Trp (SEQ ID NO: 24).

2. The VABP of claim 1, that is obtained from blood-feeding ectoparasites, spiders, scorpions, snakes or venomous animals.

3. The VABP of claim 1, wherein the VABP is obtained from ticks.

4. The VABP of claim 3, wherein the VABP is obtained from the ticks *Rhipicephalus appendiculatus* or *Dermacenter reticularis*.

5. A VABP as in any one of claims 1–4 in which the VABP specifically binds histamine.

6. The VABP of claim 1 that is bound to a resin support.

7. The vasoactive amine binding protein (VABP) of claim 1 for use in the detection of vasoactive amines in humans or animals.

8. The vasoactive amine binding protein (VABP) of claim 1 for use in the detection of histamine in humans or animals.

9. An anti-histamine method of treatment, comprising administering the VABP of claim 1 as an anti-histamine agent to a human or animal in need thereof.

10. An anti-inflammatory method of treatment, comprising administering the VABP of claim 1 as an anti-inflammatory drug to a human or animal in need thereof.

11. A pharmaceutical composition, comprising the vasoactive amine binding protein (VABP) of claim 1 in conjunction with a pharmaceutically-acceptable carrier for the treatment of inflammation in humans or animals.

12. A vasoactive amine binding protein (VABP) that binds to vasoactive amines with a dissociation constant of less than $10^{-7}$ M and contains a sequence motif selected from the group consisting of the motifs (Asp or Glu)-Ala-Trp-(Lys or Arg) (SEQ ID NO:23) and motif (Tyr or Cys)-(Glu or Asp)-(Leu or Ile)-Trp (SEQ ID NO:24).

13. The vasoactive amine binding protein (VABP) of claim 12, wherein said sequence motif is the motif (Asp or Glu)-Ala-Trp-(Lys or Arg) (SEQ ID NO:23).

14. The vasoactive amine binding protein (VABP) of claim 12, wherein said sequence motif is the motif (Tyr or Cys)-(Glu or Asp)-(Leu or Ile)-Trp (SEQ ID NO:24).

15. A kit suitable for the demonstration and quantification of histamine levels in a sample of a human or animal, comprising:

(a) the vasoactive amine binding protein (VABP) of claim 1; and (b) radiolabeled histamine, an anti-VABP antibody, or an enzyme for quantifying histamine in the sample.

16. The kit of claim 15, wherein the enzyme is selected from the group consisting of an alkakine phosphatase, a peroxidase, and a luciferase.

17. The kit if claim 15, wherein the sample is selected from the group comprising blood, nasal lavage fluid, or tissue.

* * * * *